(12) United States Patent
Poduslo et al.

(10) Patent No.: US 7,371,365 B2
(45) Date of Patent: May 13, 2008

(54) METHODS FOR DETECTING PARENCHYMAL PLAQUES IN VIVO

(75) Inventors: Joseph F. Poduslo, Rochester, MN (US); Geoffrey L. Curran, Rochester, MN (US); Thomas M. Wengenack, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 691 days.

(21) Appl. No.: 10/351,777

(22) Filed: Jan. 27, 2003

(65) Prior Publication Data

US 2004/0022736 A1 Feb. 5, 2004

Related U.S. Application Data

(63) Continuation-in-part of application No. 09/542,537, filed on Apr. 4, 2000, now abandoned.

(60) Provisional application No. 60/427,821, filed on Nov. 20, 2002.

(51) Int. Cl.
*G09B 9/00* (2006.01)
*G09B 9/56* (2006.01)

(52) U.S. Cl. .................. 424/9.34; 424/9.1; 424/9.3; 424/9.341

(58) Field of Classification Search .................. 424/9.1, 424/9.3, 9.34, 9.341
See application file for complete search history.

(56) References Cited

U.S. PATENT DOCUMENTS

| | | | |
|---|---|---|---|
| 5,231,000 A | 7/1993 | Majocha et al. | |
| 5,262,332 A | 11/1993 | Selkoe | |
| 5,670,477 A | 9/1997 | Poduslo et al. | |
| 5,898,094 A | 4/1999 | Duff et al. | |
| 6,821,504 B2 | 11/2004 | Wisniewski et al. | |

OTHER PUBLICATIONS

Muller-Gartner et al. (1998) Imaging techniques in the analysis of brain function and behaviour. Trends in Biotechnology 16: 122-130.*

J.R. Ghilardi, et al., "Intra-arterial Infusion of [125I]A(beta)1-40 Labels Amyloid Deposits in the Aged Primate Brain In Vivo," NeuroReport 7(15-17):2607-2611, 1996.
J.F. Poduslo and G.L. Curran, "Polyamine Modification Increases the Permeability of Proteins at the Blood-nerve and Blood-brain Barriers," J. Neurochem. 66(4):1599-1609, 1996.
J.F. Poduslo, et al., "Molecular Targeting of Alzheimer's Amyloid Plaques for Contrast-enhanced Magnetic Resonance Imaging," Neurobiol. Dis., pp. 1-15, 2002.
S.-P. Lee, et al., "Visualization of Beta-Amyloid Plaques in a Transgenic Mouse Model of Alzheimer's Disease Using MR Microscopy Without Contrast Reagents," Magnetic Res. Med. 52:538-544, 2004.
Holcomb et al., "Nature Med.", 1998, 4:97-100.
Hsiao, et al., "Science", 1996, 274:99-102.
Maggio et al., "Proc. Natl. Acad. Sci. USA", 1992, 89(12):5462-5466.
Maggio et al., "Brain Pathol.", 6:147-162. (1996) Brain amyloid—a physicochemical perspective.
Pallitto et al., "Biochemistry", 1999, 38:3570-3578.
Poduslo, et al., "J. Neurobiol.", 1999, 39:371-382.
Poduslo et al., "J. Neurochem.", 1998, 71:1651-1660.
Poduslo and Curran, "J. Neurochem.", 1996, 67:734-741.
Poduslo and Curran, "Molec. Brain Res.", 1994, 23:157-162.
Poduslo and Curran, "Proc. Natl. Acad. Sci. USA", 1992, 89:2218-2222.
Poduslo et al., "Proc. Natl. Acad. Sci. USA", 1994, 91:5705-5709.
Reinholz et al., "Exp. Neurol.", 1999, 159:191-203.
Reinholz et al., "Exp. Neurol.", 1999, 159:204-216.
Saji, "Crit. Rev. Ther. Drug Carrier Syst.", 1999, 16(2):209-244.
Selkoe, "Science", 1997, 275:630-631.
Walker et al., "Acta Neuropathol.", 1990, 80(4):381-387.
Wengenack et al., "Brain Res.", 1997, 754:46-54.
Wengenack et al., "Brain Res.", 1997, 767:128-135.

* cited by examiner

*Primary Examiner*—Anne-Marie Falk
(74) *Attorney, Agent, or Firm*—Quarles & Brady LLP

(57) ABSTRACT

Methods for detecting parenchymal plaque deposits in the brain of a living mammal are described that include administering a polyamine modified, labeled polypeptide having specific binding affinity for the extracellular deposit, to the living mammal. Isolated β-amyloid peptides that are polyamine modified and labeled with a radioisotope or contrast agent also are described.

19 Claims, 9 Drawing Sheets
(4 of 9 Drawing Sheet(s) Filed in Color)

METHODS FOR DETECTING PARENCHYMAL PLAQUES IN VIVO

RELATED APPLICATIONS

This application is a continuation-in-part of U.S. Provisional Application 60/427,821, filed Nov. 20, 2002 and U.S. patent application Ser. No. 09/542,537 now abandoned, filed Apr. 4, 2000. These applications are incorporated by reference herein.

TECHNICAL FIELD

This invention relates to detecting extracellular deposits such as plaques in the brain of a living mammal, and more particularly to using a polyamine-modified, labeled polypeptide as a contrast agent which enables the plaques to imaged.

BACKGROUND

Alzheimer's disease is a devastating disease of the brain which results in progressive dementia, physical disability and death over a relatively long period of time. With the aging population in the United States and other countries, the number of Alzheimer's patients is rapidly rising and can accurately be characterized as a silent epidemic. Much research is being conducted to develop drugs that will slow or halt the progression of the disease, and there is hope that a vaccine or inhibitors of secretase may ultimately be developed.

One of the difficulties in managing this disease is the lack of means for its early detection and means for measuring its progression. Such means are needed to identify persons who should receive treatment and to measure the effectiveness of the treatment. An immediate problem is the need for a method which measures the progression of the disease in order to evaluate the effectiveness of the many drugs being developed.

Many techniques have been proposed for detecting and measuring the progress of Alzheimer's disease. These include cognitive tests which attempt to measure brain functions by having the patient perform different tasks. The problem with this approach is that it does not distinguish between dementia caused by Alzheimer's disease and dementia caused by other factors. In addition, the ability to measure the progression of the disease using cognitive tests is very limited.

Neurofibrillary tangles (NFTs) and neuritic plaques (NPs) are the classical neuropathological hallmarks of Alzheimer's disease. Numerous neuropathological studies indicate that the first appearance of NFTs and NPs in the hippocampal region of the brain marks the beginning of the degenerative process. Many studies have been done in which the structure of the brain has been imaged to determine structural changes that are linked to the presence and the progression of Alzheimer's disease. These include: 2-D estimates of size; measures of medical temporal lobe gray matter volume; the qualitative rating of the amount of CSF accumulating in the hippocampal fissures, the size of the suprasellar cistern; and the increased distance between the right and left uncus. None of have been particularly successful, and in fact, it has been found that profound structural changes can occur in the brain of some individuals with no cognitive impairment or other symptoms of the disease being evident.

Alzheimer's Disease (AD) is characterized neuropathologically by neuritic plaques and neurofibrillary tangles. Neuritic or senile plaques contain a dense core consisting largely of several species of amyloid-$\beta$(A$\beta$) peptide. A$\beta$ is a 39-43 amino acid peptide derived from amyloid precursor protein. A$\beta$ is highly hydrophobic and spontaneously aggregates in vitro to form $\beta$ pleated sheets. Maggio, J. E. and Mantyh, P. W., *Brain Pathol.*, 6:147-162 (1996). A$\beta$ also has been reported to be neurotoxic in vitro and in vivo. The main link between AD and A$\beta$ is based on genetic mutations that have been discovered in familial forms of AD and Down's syndrome that result in aberrant processing or increased levels and deposition of A$\beta$. Selkoe, D. J., *Science,* 275: 630-631 (1997). Furthermore, transgenic mice overexpressing the same mutations have been shown to develop amyloid deposits like those in AD as well as significant behavioral deficits. Hsiao, K., et al., *Science* 274:99-102 (1996); and Holcomb, L., et al., *Nature Med.,* 4:97-100 (1998). There also appears to be a significant correlation between amyloid burden and dementia in AD patients.

Currently, there is no definitive diagnosis for AD except by post-mortem observation of these deposits and a process of elimination of other neurodegenerative disorders.

SUMMARY

In one embodiment, the present invention is a method for detecting parenchymal plaque deposits in the brain of a living mammal. The method comprises: a) administering an amount of a polypeptide to a mammal effective to detectably bind to parenchymal plaque deposits, wherein the polypeptide is labeled with a contrast agent and is polyamine modified, and wherein the polypeptide has specific binding affinity for said deposits; and b) detecting the polypeptide bound to the deposits. The detecting step comprises acquiring nuclear magnetic resonance image data and reconstructing an image therefrom.

In a preferred embodiment, the deposits are $\beta$-amyloid plaques and the polypeptide is a $\beta$-amyloid peptide, such as $\beta$-amyloid peptide$_{1-40}$ or derivatives thereof.

In another preferred embodiment, the polyamine is putrescine.

In another embodiment, the present invention is a method for producing an image with a magnetic resonance imaging (MRI) system which indicates parenchymal plaques in the brain of a subject. Preferably, the steps comprise: a) acquiring a reference image data set of the brain with the MRI system; b) injecting into the subject's vascular system a contrast agent comprised of a labeled polypeptide having a specific binding affinity for said plaques and being polyamine modified to enhance transit through and exit from capillary endothelial cells to the brain parenchyma; c) waiting for a time period sufficient for the contrast agent to bind to said parenchymal plaques and for unbound contrast agent to diffuse in the subject; d) acquiring a contrast enhanced image data set of the brain with the MRI system; and e) reconstructing an image of the brain which indicates at each of its image pixels the difference in NMR signal magnitude between the contrast enhanced image data set and the reference image data set.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 3A-3C represent adjacent sections incubated with buffer alone (A), or $5\times10^5$ cpm of either $^{125}$I-$A\beta_{1-40}$ (B) or $^{125}$I-PUT-$A\beta_{1-40}$ (C) and processed for anti-$A\beta$ IH and emulsion autoradiography with an equal exposure time of 6 days. Scale bars, 200 µm. FIGS. 3D-3F are higher magnifications of amyloid deposits indicated by arrows in FIGS. 3A-3C. Scale bars, 50 µm.

FIGS. 4A-4C represent adjacent sections incubated with buffer alone (A), or 100 pM of either $^{125}$I-$A\beta_{1-40}$ (B) or $^{125}$I-PUT-$A\beta_{1-40}$ (C) and processed for anti-$A\beta$ IH and emulsion autoradiography with an equal exposure time of 6 days. Scale bars, 200 µm. FIGS. 4D-4F represent higher magnification of amyloid deposits indicated by arrows in FIGS. 4A-4C. Scale bars, 50 µm.

In FIGS. 5A and 5C, sections were incubated with 100 pM of either $^{125}$I-$A\beta_{1-40}$ (5A) or $^{125}$I-PUT-$A\beta_{1-40}$ (5C) in the absence of unbound putrescine. FIGS. 5B and 5D represent adjacent section incubated with 100 pM of either $^{125}$I-$A\beta_{1-40}$ (5B) or $^{125}$I-PUT-$A\beta_{1-40}$ (5D) in the presence of 10-fold excess unbound putrescine. All sections were processed for anti-$A\beta$ IH and emulsion autoradiography with an equal exposure time of 6 days. Scale bars (5A-5D), 100 µm. FIGS. 5E-5H represent higher magnification of amyloid deposits indicated by arrows in 5A-5D. Scale bars, 10 µm.

FIG. 6A is a section through medial septum processed for anti-$A\beta$ IH and emulsion autoradiography with 8 weeks of exposure exhibiting several labeled deposits. FIG. 6B is an adjacent section showing the same deposits stained with thioflavin S. FIGS. 6C and 6D represent higher magnification of deposit #2. Scale bars (6A, 6B), 100 µm; (6C, 6D), 10 µm.

DETAILED DESCRIPTION

Figure 1:
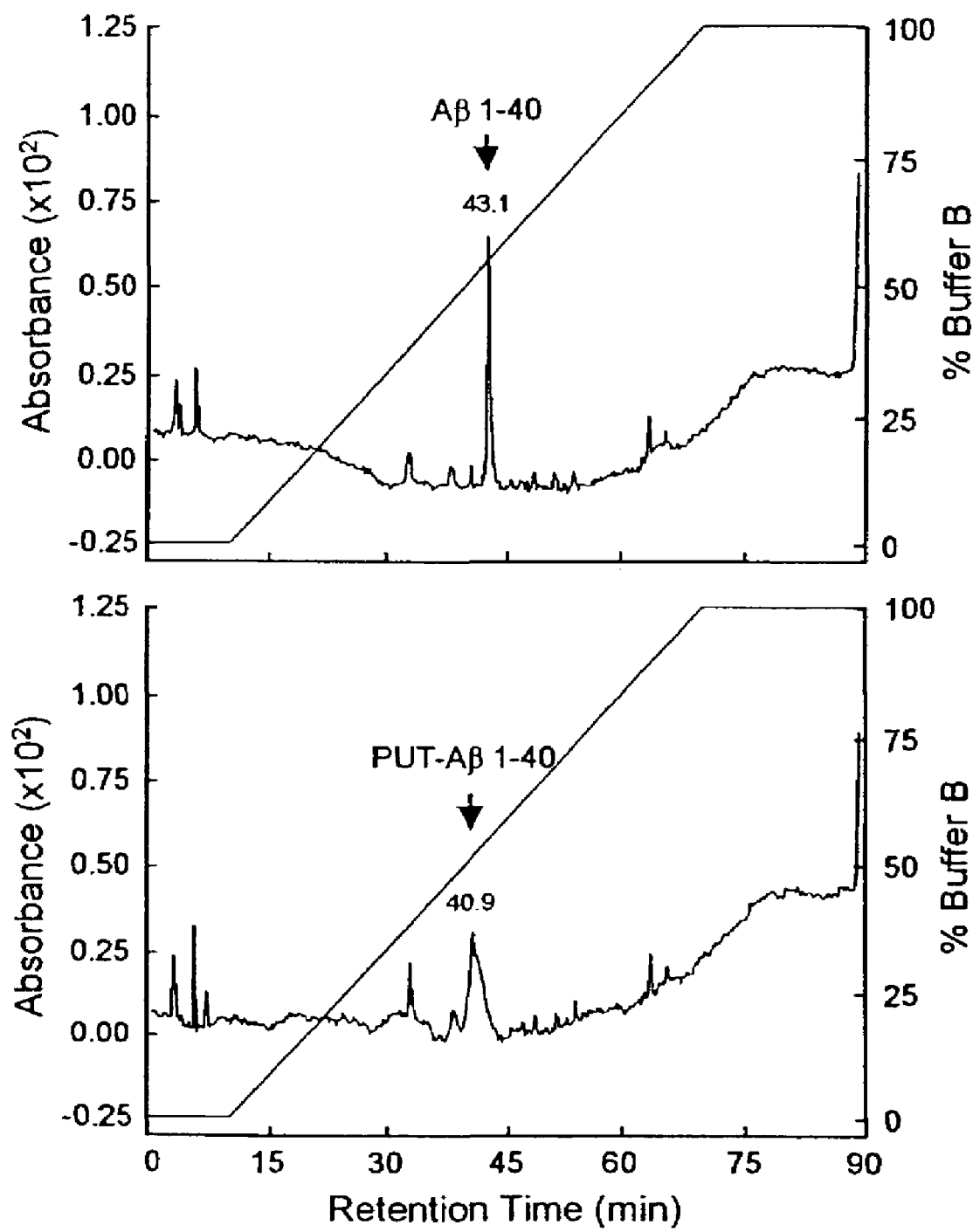
FIGS. 1A and 1B are RP-HPLC chromatograms of unlabeled $A\beta_{1-40}$ (A) and PUT-$A\beta_{1-40}$ (B). The abscissa plots the retention time in minutes. The left ordinate plots the absorbance at 214 nm. The right ordinate plots the gradient as percent of Buffer B (80% ACN/0.05% TFA/19.95% HPLC water).

The invention features a method for detecting parenchymal plaque deposits in the brain of a living mammal such as amyloid deposits, neuritic plaques, and diffuse plaques. Amyloid deposits include, for example, deposits of an $A\beta$ polypeptide or of a prion protein (PrP). In some embodiments, the methods of the invention can be used to detect tumors in the brain.

Applicants emphasize the importance of the cerebrovascular versus parenchymal amyloid plaque deposition. Cerebrovascular deposition initially occurs in the outer vessel wall of arteries and capillaries more frequently than veins. These focal amyloid deposits appear as clusters of delicate amyloid fibrils in the abluminal membrane. In more affected vessels, the amyloid forms a continuous ring within the vessel wall. As the pathology progresses, amyloid fibrils can be observed extending continuously from the endothelial cells into the neuropil.

In contrast, parenchymal amyloid plaque deposition occurs within the brain tissue itself along a continuum that includes two broad types of plaques: (1) diffuse plaques, in which $A\beta$ accumulates largely in nonfilamentous extracellular deposits-that lack altered neurites and glia, and (2) neuritic plaques, in which $A\beta$ accumulates principally in masses of extracellular filaments closely associated with dystrophic dendrites and axons, activated microglial, and reactive astrocytes.

It is important to realize that cerebrovascular deposition of amyloid can be detected in 90% of AD patients; however, cerebrovascular amyloid can occur in the absence of AD pathology and vice versa. For example, patients with hereditary cerebral hemorrhage with amyloidosis Dutch type, an autosomal-dominant severe form of cerebral amyloid angiopathy caused by a point mutation in the amyloid precursor protein, do not seem to develop significantly more amyloid plaques or neurofibrillary tangles than the normal elderly. Cerebrovascular amyloid also occurs as a sporadic disorder evident in 30% of people over 60 years of age and in 50% at age 90. The deposition of $A\beta$ in cerebral vessels leads to severe vascular pathology and is a significant risk for cerebral hemorrhage.

Methods of the invention include administering an amount of a modified polypeptide to the mammal effective to detectably bind to the extracellular deposits. The polypeptide has been modified to enhance transmit through and exit from capillary endothelial cells to the brain parenchyma. Suitable polypeptides have specific binding affinity for the extracellular deposits and are at least 10 amino acid residues in length. For example, amyloid $\beta$ peptide ($A\beta$), which has affinity for amyloid deposits, can be used. Non-limiting examples of $A\beta$ polypeptides that can be used include $A\beta_{1-40}$ and $A\beta_{1-42}$ or derivatives thereof. Beta-sheet blockers, i.e., short peptides that are homologous to the central region of $A\beta$ and include residues that inhibit beta-sheet formation (e.g., proline residues) can be used, as well as peptidyl modulators of the recognition sequence of $\beta$-amyloid aggregation. Poduslo, et al., *J. Neurobiol.*, 39:371-382 (1999). Peptidyl modulators typically are peptides that contain a portion of amino acid residues from the $A\beta$ recognition sequence (within residues 15-25 of $A\beta$ and in particular, residues KLVFF) and six lysine residues at the C-terminus as a disrupting element. Pallito, et al., *Biochemistry* 38:3570-3578 (1999). For example, the peptidyl modulator can be a peptide that includes residues 16-20 or 15-25 of Aβ with 6 lysine residues at the C-terminus. Other derivatives of amyloid precursor protein that have affinity for Aβ plaques also are suitable.

In addition, antibodies having specific binding affinity for polypeptides within the extracelluar deposits (e.g., affinity for $A\beta_{1-40}$ or $A\beta_{1-42}$, or the protease resistant form of PrP) can be used. See, U.S. Pat. No. 5,231,000 and U.S. Pat. No. 5,262,332 for examples of antibodies having specific binding affinity for Aβ. See, Zanusso, et al., *Proc. Natl. Acad. Sci. USA* 95:8812-8816 (1998) for examples of antibodies having specific binding affinity for the protease resistant form of PrP. As used herein, antibodies include polyclonal or monoclonal antibodies, humanized or chimeric antibodies, single chain Fv antibody fragments, Fab fragments, and F(ab)$_2$ fragments. Monoclonal antibodies are particularly useful. A chimeric antibody is a molecule in which different portions are derived from different animal species, such as those having a variable region derived from a murine monoclonal antibody and a human immunoglobulin constant region. Chimeric antibodies can be produced through standard techniques.

Antibody fragments that have specific binding affinity for $A\beta_{1-40}$ and $A\beta_{1-42}$ or for the protease resistant form of PrP can be generated by known techniques. Such fragments include, but are not limited to, F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed. See, for example, Huse, et al., *Science* 246:1275 (1989). Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

Labeling and Polyamine Modification of Polypeptides

Polypeptides that are administered to the living mammal are labeled and polyamine modified. The polypeptide has been modified to enhance transmit through and exit from capillary endothelial cells to the brain parenchyma. The use of a labeled peptide with greater permeability across the capillary endothelid cells increases sensitivity and allows the use of lower quantities of radioisotope. Typical labels that are useful include radioisotopes and contrast agents used for imaging procedures in humans. Non-limiting examples of labels include radioisotope such as $^{123}$I (iodine), $^{18}$F (fluorine), $^{99m}$Tc (technetium), $^{111}$In (indium), and $^{67}$Ga (gallium), and contrast agents such as, gadolinium (Gd), dysprosium, and iron. Radioactive Gd isotopes ($^{153}$Gd) also are available and suitable for imaging procedures in non-human mammals. Polypeptides can be labeled through standard techniques. For example, polypeptides can be iodinated using chloramine T or 1,3,4,6-tetrachloro-3α,6α-diphenylglycouril. For fluorination, polypeptides are synthesized and fluorine is added during the synthesis by a fluoride ion displacement reaction. See, Muller-Gartner, H., *TIB Tech.*, 16:122-130 (1998) and Saji, H., *Crit. Rev. Ther. Drug Carrier Syst.*, 16(2):209-244 (1999) for a review of synthesis of proteins with such radioisotopes.

Polypeptides also can be labeled with a contrast agent through standard techniques. For example, polypeptides can be labeled with Gd by conjugating low molecular Gd chelates such as Gd diethylene triamine pentaacetic acid (GdDTPA) or Gd tetraazacyclododecanetetraacetic (Gd-DOTA) to the polypeptide. See, Caravan, et al., *Chem. Rev.* 99:2293-2352 (1999) and Lauffer, et al., *J. Macn. Reson. Imaging* 3:11-16 (1985). Antibodies can be labeled with Gd by, for example, conjugating polylysine-Gd chelates to the antibody. See, for example, Curtet, et al., *Invest. Radiol.* 33(10):752-761 (1998). Alternatively, antibodies can be labeled with Gd by incubating paramagnetic polymerized liposomes that include Gd chelator lipid with avidin and biotinylated antibody. See, for example, Sipkins, et al., *Nature Medicine*, 4 623-626 (1998).

Polypeptides are modified with polyamines that are either naturally-occurring or synthetic. See, for example, U.S. Pat. No. 5,670,477. Useful naturally-occurring polypeptides include putrescine, spermidine, spermine, 1,3-diaminopropane, norspermidine, syn-homospermidine, thermine, thermospermine, caldopentamine, homocaldopentamine, and canavalmine. Putrescine, spermidine, and spermine are particularly useful. Synthetic polyamines are composed of the empirical formula $C_xH_yN_z$, and can be cyclic or acyclic, branched or unbranched, hydrocarbyl chains of 3-12 carbon atoms that further include 1-6 NR or N(R)$_2$ moieties, wherein R is H, (C$_1$-C$_4$) alkyl, phenyl, or benzyl. Alternatively, amino acids are synthesized with the appropriate polyamine (such as Glu-4-aminobutane or Asp-4-aminobutane) and incorporated at the appropriate sequence position during synthesis of the AB derivative.

The permeability coefficient-surface area product (PS) at the blood-brain barrier (BBB) is equivalent to the "permeability of proteins at the BBB." The PS product (permeability) is a measure of the rate of transport at the BBB. The BBB actually refers to tight junctions that exist between the capillary endothelial cells which prevent diffusion of reagents from the circulation into the brain parenchyma. Unlike capillaries in other organs, brain capillaries are unfenestrated (closed), whereas in most other organs the capillaries are fenestrated (open); that is, windows exist between the cells to allow for diffusion of reagents from circulation into the tissue of the organ. Therefore, in order for a substance to cross the BBB, it first must come in contact with the luminal surface of the capillary endothelial cell and a mechanism must exist by which this reagent is transported across this luminal membrane (that is, by means of a receptor or transporter; see Exhibit A). Once the reagent is in the endothelial cell, it must undergo transcytosis and then exit from the endothelial cell at the abluminal membrane surface by a different receptor or antiporter, where it then passes into the brain parenchyma.

As described herein, putrescine modification of $A\beta_{1-40}$ significantly increased its permeability at the blood brain barrier (BBB) an average of two-fold. Permeability at the BBB of putrescine modified and Gd labeled $A\beta_{1-40}$ also was significantly increased 1.5-2.0 fold relative to native $A\beta_{1-40}$ It should be noted that the permeability coefficient-surface area product (PS) values for $A\beta_{1-40}$ are relatively high already and compare to that of insulin, whose PS value in rat cortex is $15.78 \times 10^{-6}$ ml/g/s, and BBB uptake is known to occur by receptor-mediated transport. Poduslo, J. F., et al., *Proc. Natl. Acad. Sci. USA* 9:5705-5709 (1994). As a basis for comparison, the PS value for albumin in rat cortex is $0.15 \times 10^{-6}$ ml/g/s, and is thought to cross the BBB by passive diffusion. The high PS value for $A\beta_{1-40}$ coupled with stereospecific BBB permeability data for L-$A\beta_{1-40}$ indicate that the BBB transport likely occurs by a receptor-mediated mechanism. Thus, a doubling of the already high PS value for $A\beta_{1-40}$ by putrescine modification represents a further dramatic increase in its permeability at the BBB with important physiological implications for enhanced delivery into the CNS.

There are many approaches for the chemical cross-linking or "linkage" of polypeptides to polyamines. Significant advancement in the application of these cross-linking agents has led to the synthesis of cleavable bifunctional compounds. There are over 300 cross-linkers now available. It is desirable that the linkage of polypeptide to polyamine allows the polypeptide to maintain the ability to bind the extracellular deposit and the polyamine to facilitate increased permeability at the BBB.

Numerous considerations, such as reactivity, specificity, spacer arm length, membrane permeability, cleavability and solubility characteristics need to be evaluated when choosing an appropriate cross-linker. See, for example, "Chemistry of Protein Conjugation and Cross-Linking", Shan S. Wong, CRC Press, Ann Arbor, 1991. Functional groups that are available for conjugation are not involved in the binding of the polypeptide to the extracellular deposit.

Linking reagents have at least two reactive groups and can be either homobifunctional with two identical reactive groups or heterobifunctional with two or more different reactive groups. Trifunctional groups also exist and can contain three functional groups. Most homobifunctional cross-linkers react with primary amines commonly found on proteins. Other homobifunctional cross-linkers couple through primary sulfhydryls. Homobifunctional cross-linkers can be used in a one step reaction procedure in which the compounds to be coupled are mixed and the cross-linker is added to the solution. The resulting cross-linking method may result in self-conjugation, intermolecular cross-linking, and/or polymerization. The following are examples of cross-linking approaches and are not meant to be inclusive.

Imido esters are the most specific acylating reagents for reaction with amine groups whereby in mild alkaline pH, imido esters react only with primary amines to form imidoamides. The product carries a positive charge at physiological pH, as does the primary amine it replaces and therefore, does not affect the overall charge of the protein.

Homobifunctional N-hydroxysuccinimidyl ester conjugation is also a useful cross-link approach to crosslink amine-containing proteins. Homobifunctional sulfhydryl reactive cross-linkers include bismaleimidhexane (BMH), 1,5-difluoro-2,4-dinitrobenzene (DFDNB), and 1,4-di-(3',2'-pyridyidithio) propionamido butane (DPDPB).

Many heterobifunctional cross-linkers are commercially available with the majority containing an amine-reactive functional group on one end and a sulfhydryl-reactive group on the other end. Multiple heterobifunctional haloacetyl cross-linkers are available, as are pyridyl disulfide cross-linkers. Carbodiimides are a classic example of heterobifunctional cross-linking reagents for coupling carboxyls to amines resulting in an amide bond.

Administration of Labeled, Polyamine Modified Polypeptides

The labeled, polyamine modified polypeptides are formulated with a pharmaceutically acceptable carrier and administered to the living mammal. In general, the polypeptides are administered intravenously (i.v.), although other parenteral routes of administration, including subcutaneous, intramuscular, intrarterial, intracarotid, and intrathecal also can be used.

Formulations for parenteral administration may contain pharmaceutically acceptable carriers such as sterile water or saline, polyalkylene glycols such as polyethylene glycol, vegetable oils, hydrogenated naphthalenes, and the like.

The dosage of labeled, polyamine modified polypeptide to be administered will be determined by the attending physician taking into account various factors known to modify the action of drugs. These include health status, body weight, sex, diet, time and route of administration, other medications, and any other relevant clinical factors. Typically, about 1-3000 μg/kg body weight are administered. For example, the dosage can range from about 10-1000 μg/kg body weight or 50-500 μg/kg body weight. Therapeutically effective dosages may be determined by either in vitro or in vivo methods.

Detecting Polypeptides Bound to Extracellular Deposits

Imaging techniques that can be used to detect labeled deposits include positron emission tomography (PET), gamma-scintigraphy, magnetic resonance imaging (MRI), functional magnetic resonance imaging (FMRI), magnetoencephalography (MEG), and single photon emission computerized tomography (SPECT). Such imaging techniques can be used to detect labeled deposits in vitro or in vivo.

MRI is a particularly useful imaging technique, as the spatial resolution (e.g., 30 microns) and signal-to-noise ratio provided by MRI are suitable for detecting amyloid deposits in a sample. Any type of MRI data set can be acquired from a sample, including T1 or T2 images (e.g., a T1-weighted (T1W) or T2-weighted (T2W) image). Areas that contain plaques can be visualized in bulk relative to a control region of the brain. That is, instead of looking at individual plaques, regions of the brain that typically contain plaques can be examined as a whole. Areas in the brain of AD patients that typically contain plaques include the limbic cortex and heteromodal association cortices. Areas in the brain of an AD patient that typically remain free of plaque deposition can be used as control regions. Such regions include the cerebellum, the primary occipital cortex, and the primary sensory motor cortex. To detect plaques, the average signal intensity of each region can be compared. For example, T1 images of the limbic cortex and cerebellum can be obtained and the average signal intensity determined for each region. An increase in signal intensity in the limbic cortex relative to that in the cerebellum would indicate that plaques are present. Comparing the signal intensities of the two regions provides a useful measure of regional plaque density, plaque distribution within the bulk tissue, as well as Alzheimer's disease progression within the patient.

Individual labeled deposits also can be detected by comparing the signal intensity of a region bounding a suspected plaque relative to that of a region adjacent to the plaque. With a T2 weighted image, the average signal intensity of a labeled plaque is typically reduced relative to the average signal intensity in a region adjacent to the plaque. With a T1 weighted image, the average signal intensity of a labeled plaque is typically elevated when compared to average signal intensity in a region adjacent to the plaque.

It is understood that parameters such as voxel size and magnetic field strength can be optimized when detecting extracellular deposits using MRI. Additional parameters and methods of optimization are known in the art. For example, a voxel volume of $1.25\times10_5$ to $1.0\times10^6$ cubic microns (i.e., $1.25\times10^5$, $1.5\times10^5$, $2.0\times10^5$, $5.0\times10^5$, or $1.0\times10_6$ cubic microns) and a high magnetic field strength (e.g., 7 tesla or greater) can be used to improve the resolution and detection of individual labeled plaques in the brain in vivo. Motion correction techniques also can be used to further improve data sets obtained using in vivo MRI.

Figure 7:
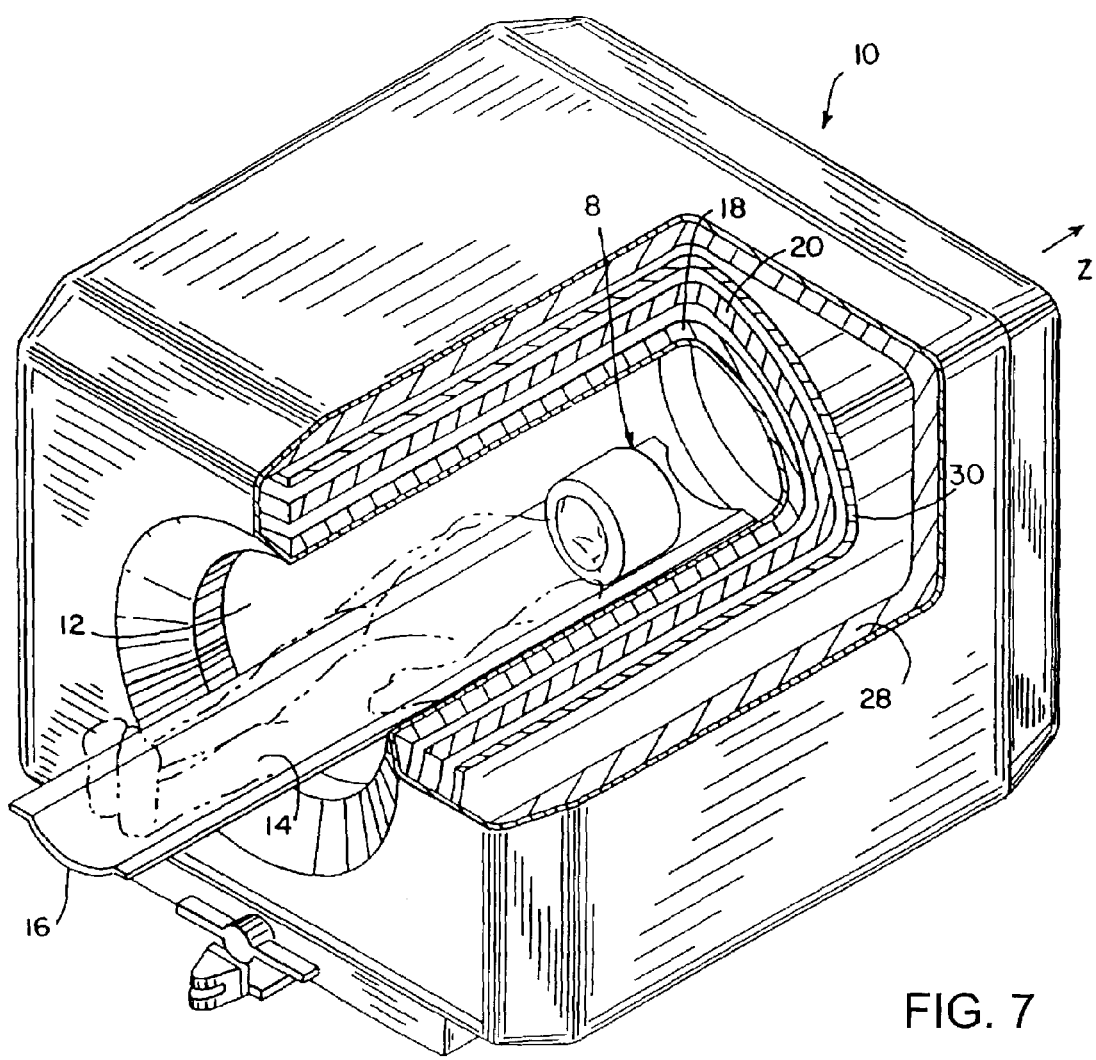
FIG. 7 is a pictorial representation of an NMR system used to practice the present invention.

Referring to FIG. 7, an MRI magnet assembly 10 has a cylindrical bore tube 12 extending along a z-axis 13 for receiving a supine patient 14 supported on a table 16. The table 16 may move in and out of the bore tube 12 so as to position the patient 14 along the z-axis 13 within the volume of the bore tube 12.

Coaxially surrounding the bore tube 12 is a whole-body RF coil 18 for exciting the spins of the patient 14 into resonance. Whole-body gradient coils 20 surround both the bore tube 12 and the RF coil 18 and are also coaxial with the z-axis 13, to provide x, y and z gradient fields $G_x$, $G_y$, and $G_z$ as required for MRI imaging. The gradient coils 20 are driven by gradient amplifiers (not shown). The polarizing magnetic field $B_0$, aligned with the z-axis 13 is generated by a superconducting magnet coil 28 coaxial with but outside the bore tube 12, the RF coil 18 and the gradient coils 20. The superconducting magnet coil 28 has no external power supply but operates on an initial current which continues unabated in the zero resistivity windings of the superconducting magnet coil 28.

Interposed between the superconducting magnet coil 28 and the gradient coil 20 is a set of shim coils 30 which are used to correct the homogeneity of the polarizing field $B_0$ as is understood in the art. A set of mechanical linkages and insulators (not shown) rigidly connect each of these coils 18, 20, 28 and 30 together to the bore tube 12 so as to resist relative motions generated by the interaction of their various electromagnetic fields.

When a local coil assembly 8 is used in a general purpose system such as that described above, the whole-body gradient coils 20 and whole-body RF coil 18 are disconnected. The local coil assembly 8 is connected to the x, y and z gradient amplifiers (not shown) on the NMR system and it is connected to the system's transceiver through a transmit/receive switch. The preferred embodiment employs a 3 Tesla MRI system manufactured by Bruker Analytische MeBtechnik GmbH and sold under the trademark BIOSPEC 30/60.

Because the gradient fields are switched at a very high speed to practice the preferred embodiment of the invention, local gradient coils are employed in place of the whole-body gradient coils 139. These local gradient coils are designed for the head and are in close proximity thereto. This enables the inductance of the local gradient coils to be reduced and the gradient switching rates increased. The local gradient coil assembly 8 also includes a local brain RF coil. In the preferred embodiment, it is a 16 element bandpass end-capped birdcage coil. This brain RF coil is designed to couple very efficiently to the brain of the subject and less efficiently to the lower part of the head. This results in improved brain image quality compared with larger general purpose head coils that couple uniformly to the entire head as well as the neck. An RF shield surrounds the local brain coil and interior to the local gradient coil. This shield isolates RF radiation from the local gradient coil. The shield is designed to avoid perturbation of time varying gradient fields. For a description of these local gradient coils and the RF coil which is incorporated herein by reference, reference is made to U.S. Pat. No. 5,372,137 filed on Jan. 19, 1993 and entitled "NMR Local Coil For Brain Imaging".

Figure 8:
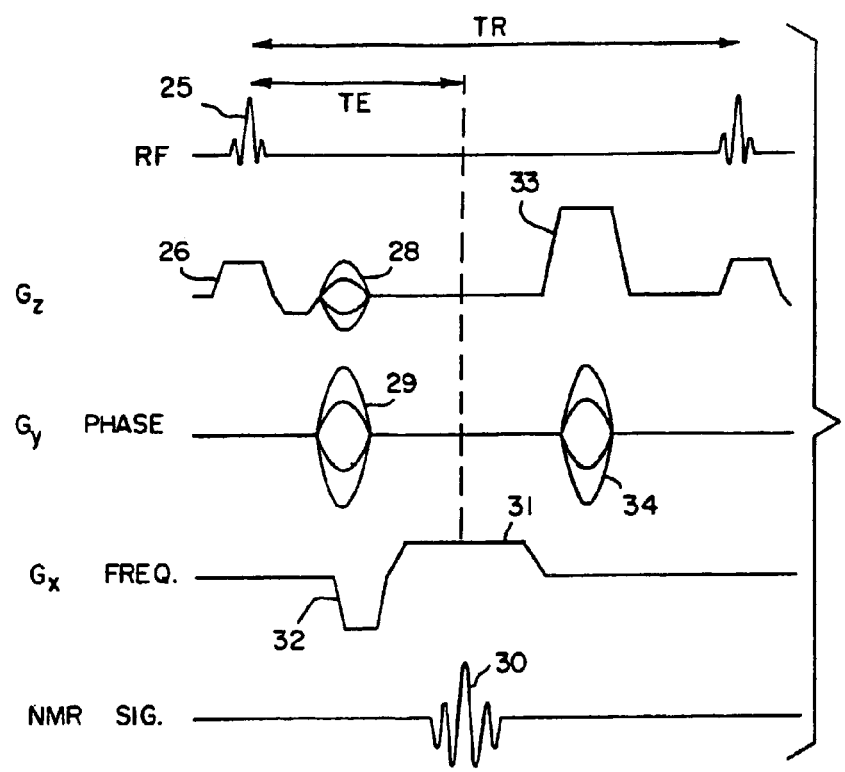
FIG. 8 is a graphic representation of a 3D gradient recalled echo pulse sequence used to acquire image data according to a preferred embodiment of the invention.

The MRI system of FIG. 7 performs a series of pulse sequences to collect sufficient NMR image data to reconstruct an image. Referring particularly to FIG. 8, an exemplary pulse sequence for conducting a 3DFT NMR scan is shown. The pulse sequence commences by the selective excitation of the entire region of interest with an RF excitation pulse 25 in the presence of a slab select $G_z$ gradient pulse 26. The frequency content of the excitation pulse 25 and the amplitude of the slab select $G_z$ pulse 26 are selected to produce transverse magnetization in the region of the subject's brain which is the subject of the 3D scan. A negative $G_z$ pulse 27 is then produced to rephase the spins in preparation for the phase encoding and readout.

Phase encoding is performed along two axes: the z-axis and the y-axis. The z-axis encoding is accomplished by applying a $G_z$ phase encoding pulse 28 and the y-axis encoding is accomplished by applying a $G_y$ phase encoding pulse 29. As is well-known to those skilled in the art, the magnitude of the phase encoding pulses 28 and 29 are stepped through a series of positive and negative values during the scan, but each is set to one value during each pulse sequence.

After phase encoding the transverse magnetization, the NMR signal 30 is read-out and acquired in the presence of a $G_x$ read-out gradient 31. This read-out is preceded by a negative $G_x$ gradient pulse 32 to produce the gradient refocused NMR echo signal 30 in the usual fashion. The 3DFT pulse sequence is then concluded by the application of a large $G_z$ spoiler gradient pulse 33 and a $G_y$ rewinder gradient pulse 34 to prepare the magnetization for the next pulse sequence which follows. As is known to those skilled in the art, the spoiler pulse 33 dephases transverse magnetization and the rewinder pulse 34 refocuses transverse magnetization along the y-axis in preparation for the next pulse sequence. The rewinder pulse 34 is equal in magnitude, but opposite in polarity with the $G_y$ phase encoding pulse 29. The scan parameters of the pulse sequence are selected to acquire a very high resolution (e.g., 1 mm cubic voxels) T1 weighted image of a selected 3D volume of the subject's brain.

Contrast enhanced examinations are performed routinely in clinical brain MRI studies. The agents used are biologically stable gadolinium chelates such as gadolinium diethylenetriaminepentaacetic acid (Gd-DTPA). The NMR signal 30 acquired by the pulse sequence is produced by water protons, or "spins" which are omnipresent in the tissue. Gd-DTPA accelerates the T1 relaxation rate of nearby spins in direct proportion to its concentration in tissue. In concentrations used in clinical studies, the T1 acceleration effort of Gd-DTPA is substantially more pronounced than T2 acceleration. The basis for visualization of β-amyloid plaques using contrast enhanced MRI is the acceleration of the T1 relaxation rate of tissue water protons in the vicinity of β-amyloid plaques that have been specifically targeted by the gadolinium tagged molecular probe.

The ideal MRI contrast agent for visualizing and quantifying the pathologic burden of β-amyloid plaque has four properties: 1) it is highly stable in vivo, 2) it crosses the BBB nondestructively following intravenous injection, 3) it binds to parenchymal amyloid plaques with high affinity, and 4) it produces local changes in tissue contrast detectable by MRI. We have demonstrated that these properties exist in putrescine-gadolinium-amyloid-β peptide (PUT-Gd-Aβ).

Figure 9:
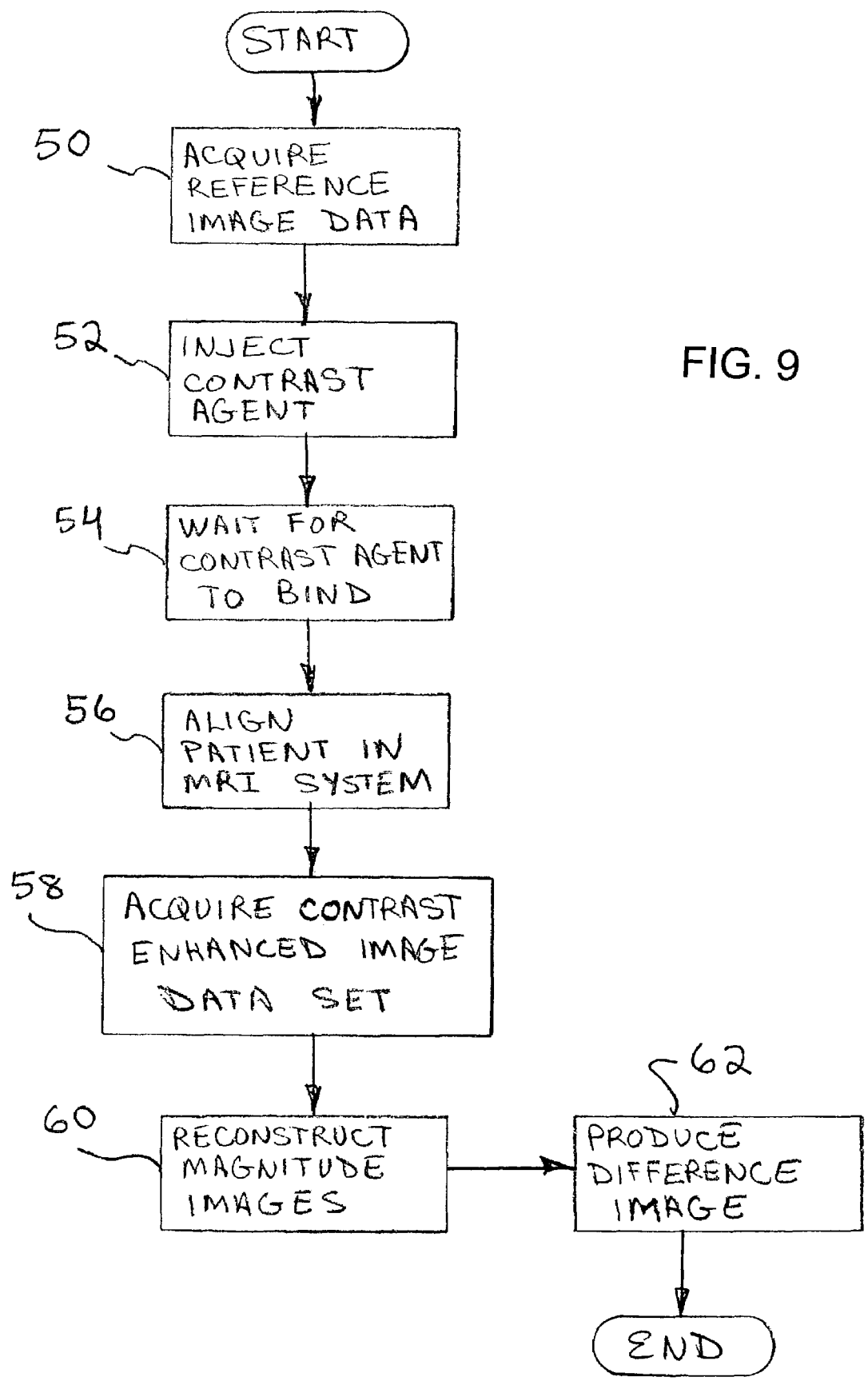
FIG. 9 is a flow chart illustrating the steps for practicing a preferred embodiment of the invention.

Referring particularly to FIG. 9, the imaging method according to a preferred embodiment of the invention includes the acquisition of a reference image as indicated at process block 50. This employs the MRI system of FIG. 7 and the pulse sequence of FIG. 8. The scan parameters are identical to those to be used in subsequent contrast enhanced image acquisition. The purpose of this reference acquisition is to produce an image that is not contrast enhanced. As indicated at process block 52, the subject is then injected with a contrast agent. This is done using a GdDTPA contrast agent conjugated to a polypeptide and modified with polyamines as described in detail above.

As indicated at process block 54, a substantial waiting period is then required before the procedure can continue. During this waiting period the contrast agent penetrates the BBB as described above and binds to parenchymal amyloid plaques in the brain. The contrast agent remains bound to plaque for many hours and a waiting period is required to dissipate the unbound contrast agent which is flowing throughout the subject's vasculature. This is substantially different from prior contrast enhanced MRI brain studies where image acquisitions are timed for peak contrast agent concentration in the vasculature. In the present method sufficient time must be allowed to pass such that signals from untargeted spins are no longer significantly enhanced by the contrast agent.

The lengthy waiting period usually requires that the subject be removed from the MRI system for a period of time. When the waiting period is over, the subject is placed back in the MRI system and aligned in the exact same position and orientation with respect to the MRI system imaging gradient coordinates as indicated at process block 56. While this can be done with a great deal of precision by physically aligning the subject, because very high resolution images are being acquired, a more precise alignment method is preferred. More particularly, a spherical 3D reference navigator signal is acquired with the reference image data set and another spherical 3D navigator signal is now acquired after the subject is repositioned. As described in co-pending U.S. patent application (MMV-01-160) filed on Dec. 19, 2002 and entitled "Alignment Of Multiple MR Images Using Navigator Signals" the MRI imaging gradient coordinates are rotated and translated as necessary to precisely register subsequently acquired images with previously acquired reference images.

As indicated at process block 58, after the subject is properly aligned, a contrast enhanced image data set is acquired using the pulse sequence in FIG. 8. The scan parameters are identical to those used to acquire the reference image data set. Both 3D image data sets are then Fourier transformed along each of their three axes and two corresponding magnitude images are produced as indicated at process block 60. The 3D reference magnitude image indicates pre-contrast NMR signal strength at each of its pixels, and the 3D contrast enhance magnitude image indicates NMR signal strength at corresponding pixels after the contrast agent has bound to plaques.

As indicated at process block 62, the reference magnitude image is then subtracted on a pixel-by-pixel basis from the contrast enhanced magnitude. The resulting difference image indicates the location and magnitude of signal enhancement due to contrast agent. Since the targeted contrast agent only binds to plaques, the difference image indicates the location of bulk tissue enhancement due to plaques in the 1 mm cubic voxel that corresponds to the 3D image pixels.

To confirm that the targeted contrast agent only binds to plaques and that the difference in image intensity corresponds to plaque locations, a number of experiments have been performed as described in the examples below.

MRI was performed at a magnetic field strength of 7 Tesla with a Bruker Avance DRX-300, 89-mm vertical bore spectrometer at an ambient temperature of 22° C. The glass tube containing embedded mouse brain was placed into a 10 mm diameter RF coil. T1-weighted (T1W) and T2-weighted (T2W) imaging sequences were performed with the following parameters: field of view of 1.6 cm along the z (vertical magnet) axis and 0.8 cm along the other two orthogonal axes; data acquisition matrix size of 256 (along the z axis)×128×128 resulting in cubic voxels 62.5 µm in all dimensions. The signal was read along the z-axis direction at a bandwidth of 50 kHz. A T2W image volume with TR=3000 ms and TE=100 ms was obtained in 13 hours, 52 minutes. A T1W image volume with TR=400 ms and TE=8 ms and 8 signal averages was obtained in 14 hours, 42 minutes.

Histological correlation was performed following MRI. Briefly, the bottom of the glass MRI tube was cut off and the hemisphere-containing agar extruded. The agar was then carefully cut away from the hemisphere. A 5 mm thick block of agar was left attached to the posterior of the hemisphere as a base for mounting to the microtome platform to maintain the same orientation of the hemisphere as in the MRI scan. After cryoprotecting in sucrose, frozen coronal sections (30 µm) of each hemisphere were cut with a sliding microtome throughout the entire cerebral cortex. All sections were saved and stored at 4° C. in a PBS solution containing 2 mM sodium azide until mounted. Every other section was mounted on gelatin-subbed slides and dried overnight at 37° C. The dried sections were stained with fresh, filtered, aqueous 1% thioflavin S, a fluorescent dye that stains neuritic-type β-amyloid plaques. The thioflavin S-positive β-amyloid deposits were visualized in the sections using a confocal laser scanning microscope (Zeiss LSM 310) equipped with a 2.5× objective at a zoom setting of 0.8 to fit the entire section of hemisphere within the field of view. Confocal images were obtained using an argon/krypton laser and settings for fluorescein isothiocyanate (FITC) at an excitation wavelength of 488 nm and emission of 520 nm. Images were saved as digitized TIFF files to retain maximum resolution. Images of the individual histologic sections were combined to create a digitized three-dimensional (3D) volume of the specimen using ANALYZE image analysis software version. See, for example, Robb, R. A., in "3D Imaging in Medicine", K. H. Hohne, S. M. Pizer, Eds. (NATO ASI Series, 1990) pp. 333-361. The 3D T2W MRI volume was then spatially matched to the digitized histologic volume using common anatomic landmarks, e.g., the anterior commissure. The rigid-body transformation matrix derived from the anatomic matching procedure was saved and applied to both the T2W and T1W MRI volumes, which were resampled in the space of the digitized histologic volume using sinc interpolation. The T2W and T1W MRI volumes were in perfect spatial registration with each other a priori because the geometric parameters of the T1W and T2W acquisition protocols were identical.

EXAMPLES

Example 1

PS and $V_p$ Measurements of Radioiodinated AβProteins

Permeability of $Aβ_{1-40}$ or PUT-$Aβ_{1-40}$ at the BBB was determined using an i.v. bolus injection technique that has been described in detail. Poduslo, J. F. and Curran, G. L., Proc. Natl. Acad. Sci. USA 89:2218-2222 (1992); Poduslo, J. F. and Curran, G. L., Molec. Brain Res. 23:157-162 (1994); and Poduslo, J. F., et al., Proc. Natl. Acad. Sci. USA 9:5705-5709 (1994). Putrescine modification of synthetic human $A\beta_{1-40}$ was performed by covalent linkage of the polyamine to carboxylic acid groups using carbodiimide at a pH of 6.7. Poduslo, J. F. and Curran, G. L., J. Neurochem. 66:1599-1609 (1996); and Poduslo, J. F. and Curran, G. L., J. Neurochem. 67:734-741 (1996).

Separate aliquots of native (Aβ 1-40) or putrescine-modified (PUT-Aβ 1-40) peptides then were labeled with $^{125}$I and $^{131}$I (Amersham) using a modified chloramine-T procedure. PS and $V_p$ values were determined in normal adult male Sprague-Dawley rats (400-450 g) obtained from Harlan. All procedures performed were in accordance with NIH Guidelines for the Care and Use of Laboratory Animals. Briefly, a bolus of 0.9% NaCl containing $A\beta_{1-40}$ or PUT-$A\beta_{1-40}$ labeled with $^{125}$I was injected rapidly into the catheterized brachial vein of an anesthetized rat (sodium pentobarbital, 25 mg/kg, i.p.). Blood (200 μl) was sampled from the brachial artery at several intervals during the next 15 minutes. An aliquot of the peptide labeled with $^{131}$I was then injected into the brachial vein 15 seconds prior to sacrifice of the animal to serve as a measure of residual plasma volume ($V_p$; μl/g). After collection of the final blood sample, the anesthetized animal was sacrificed. Several brain regions and plasma samples were assayed for $^{125}$I and $^{131}$I radioactivity in a two-channel gamma counter (Cobra II, Packard) with the activity corrected for background and crossover of $^{131}$I activity into the $^{125}$I channel. The permeability coefficient x surface area products (PS; $10^{-6}$ ml/g/s) for $A\beta_{1-40}$ and PUT-$A\beta_{1-40}$ were calculated using the $V_p$ (μl/g) as a measure of residual plasma volume. Statistical evaluations of PS and $V_p$ were performed using ANOVA followed by Bonferroni multiple comparisons.

Putrescine-modified $A\beta_{1-40}$ (PUT-$A\beta_{1-40}$) exhibited increased permeability at the BBB compared to native $A\beta_{1-40}$. Putrescine modification significantly increased the BBB permeability of PUT-$A\beta_{1-40}$ in all brain regions measured, compared to $A\beta_{1-40}$, with significant increases in the permeability coefficient x surface area product (PS) ranging from 1.9-fold in the hippocampus and cerebellum to 2.3-fold in the cortex and thalamus (Table 1). The residual plasma volume ($V_p$) was increased slightly, but significantly in three of six brain regions (Table 1). This was probably a result of the large increases in the PS values observed for PUT-$A\beta_{1-40}$, with some of the peptide crossing the BBB even in the short time used in this experiment for the administration of the second isotope (15 seconds).

TABLE 1

PS and Vp of $A\beta_{1-40}$ and PUT $A\beta_{1-40}$

| Brain Region | PS | | | Vp | | |
|---|---|---|---|---|---|---|
| | Aβ 1-40 | PUT Aβ 1-40 | RI | Aβ 1-40 | PUT Aβ 1-40 | RI |
| Cortex | 10.9 ± 0.6 | 25.5 ± 3.2 | 2.3*** | 9.4 ± 0.4 | 13.9 ± 0.7 | 1.5** |
| Caudoputamen | 12.8 ± 0.7 | 26.0 ± 3.4 | 2.0*** | 6.6 ± 0.4 | 9.2 ± 0.8 | 1.4** |
| Hippocampus | 12.7 ± 1.4 | 24.3 ± 2.9 | 1.9*** | 8.6 ± 1.4 | 10.1 ± 0.5 | 1.2 |
| Thalamus | 13.4 ± 0.7 | 30.2 ± 3.2 | 2.3*** | 12.2 ± 0.6 | 11.1 ± 0.3 | 0.9 |
| Brain Stem | 17.7 ± 1.2 | 35.1 ± 5.3 | 2.0*** | 16.2 ± 1.2 | 25.5 ± 1.7 | 1.6*** |
| Cerebellum | 18.2 ± 1.5 | 34.8 ± 4.1 | 1.9*** | 12.4 ± 0.8 | 15.1 ± 0.8 | 1.2 |

PS is the permeability coefficient x surface area product (mean ± SEM x $10^{-6}$ ml/g/s; n = 10).
Vp is the residual plasma volume (mean ± SEM μl/g; n = 10).
RI is the relative increase of PUT $A\beta_{1-40}$ compared to $A\beta_{1-40}$.
*$p < 0.05$,
**$p < 0.01$,
***$p < 0.001$.

Example 2

Labeling of Amyloid Plaques In Vitro

The next step was to determine if PUT-$A\beta_{1-40}$ would bind and label amyloid deposits in AD brain sections in vitro. $A\beta_{1-40}$ and PUT-$A\beta_{1-40}$ were first radiolabeled with $^{125}$I to facilitate detection and then purified to remove unbound $^{125}$I and unlabeled peptide. Radioiodinated $A\beta_{1-40}$ and PUT-$A\beta_{1-40}$ were purified using reversed-phase high performance liquid chromatography (RP-HPLC) to remove iodotyrosine and unlabeled peptide in order to achieve very high specific activity. Maggio, J. E., et al., Proc. Natl. Acad. Sci. USA 89:5462-5466 (1992); and Ghilardi, J. R. et al. NeuroReport 7:2607-2611 (1996). Following radioiodination, the peptides were dialyzed for 4 hours against 0.2 M NaI to remove unbound $^{125}$I. The peptides were then passed over a $C_{18}$ preparative cartridge (Sep-Pak Light, Waters Corp.) to remove more unbound $^{125}$I. The peptide was eluted stepwise with increasing concentrations of acetonitrile (ACN) in 0.05% trifluoroacetic acid (TFA) (10, 20, 40, 80, 100% ACN, Fisher). The peptides eluted primarily in the 40 and 80% ACN fractions and were reduced by adding 2-mercaptoethanol (2-ME, Bio-Rad). The peptides were concentrated to 0.25 ml with a Speed Vac (Savant).

The $^{125}$I-$A\beta_{1-40}$ and $^{125}$I-PUT-$A\beta_{1-40}$ were purified by RP-HPLC (System Gold, Beckman) using a gradient method with a binary solvent system (Buffer A: 0.05% TFA/99.95% water; Buffer B: 80% ACN/0.05% TFA/19.95% water). Each peptide was injected and purified using a 1-hour gradient of 0-100% Buffer B at a rate of 1 ml/min using a small-bore, $C_{18}$ column (5 μm, 4.6×250 mm, #218TP54, Vydac). Chromatograms of HPLC elution profiles of unlabeled $A\beta_{1-40}$ and PUT-$A\beta_{1-40}$ are shown in FIGS. 1A and 1B, respectively. PUT-$A\beta_{1-40}$ elutes earlier than $A\beta_{1-40}$ because the positively charged amine groups of putrescine make PUT-$A\beta_{1-40}$ less hydrophobic. One-minute (1 ml) fractions were collected with the detector turned off so as not to quench any of the radioactivity. Aliquots (5 μl) of ten fractions surrounding the most radioactive fraction were then counted with the gamma counter to identify the fraction with the highest radioactivity. That fraction containing the purest $^{125}$I-labeled peptide was then concentrated to 0.25 ml with a Speed Vac to remove the ACN and stored at −20° C. in the presence of a reducing agent (2-ME). Aliquots of the RP-HPLC fractions presumed to contain the $^{125}$I-A$\beta_{1-40}$ and $^{125}$I-PUT-A$\beta_{1-40}$ were analyzed by SDS-polyacrylamide gel electrophoresis (SDS-PAGE). Only a single band was observed for all fractions of $^{125}$I-A$\beta_{1-40}$ and $^{125}$I-PUT-A$\beta_{1-40}$, verifying their purity.

HPLC purified $^{125}$I-A$\beta_{1-40}$ and $^{125}$I-PUT-A$\beta_{1-40}$ were incubated with adjacent sections of unfixed AD temporal lobe cortex. Three adjacent sections were incubated with either $^{125}$I-A$\beta$ 1-40, $^{125}$I-PUT-A$\beta$ 1-40, or vehicle. Briefly, the sections were first blocked with 0.1% bovine serum albumin (BSA) in 0.05 M Tris HCl/0.9% NaCl (TBS), pH 7.0 for 30 minutes. The sections were then incubated for 3 hours with 100 pM $^{125}$I-A$\beta_{1-40}$ or $^{125}$I-PUT-A$\beta$ 1-40, or alone in 250 µl of TBS, pH 7.0 containing 0.1% BSA, 0.6 mg/ml magnesium chloride, 0.04 mg/ml bacitracin, 0.002 mg/ml chymostatin, and 0.004 mg/ml leupeptin. The sections were washed with TBS, pH 7.0 four times and then rinsed briefly with distilled water twice. The sections were allowed to air dry overnight in a box with desiccant at 4° C.

Sections then underwent immunohistochemistry (IH) for amyloid using an anti-A$\beta$ monoclonal mouse antibody (4G8, Senetek). Untreated sections were included as a positive control for antibody staining. After rehydrating with TBS, pH 7.6, the sections were fixed briefly with neutral-buffered, 10% formalin for 3 minutes. The sections were washed with TBS and then blocked with 1.5% normal horse serum in TBS for 30 minutes. The sections were incubated with the anti-A$\beta$ primary antibody at a dilution of 1:1000 in 0.1% BSA/TBS overnight at 4° C. The primary antibody was then visualized using a Vectastain Elite ABC, immunoperoxidase kit with diaminobenzidine (DAB) as a substrate according to the instructions (Vector Laboratories). The sections were allowed to air dry overnight in a box with desiccant at 4° C.

Figure 2:
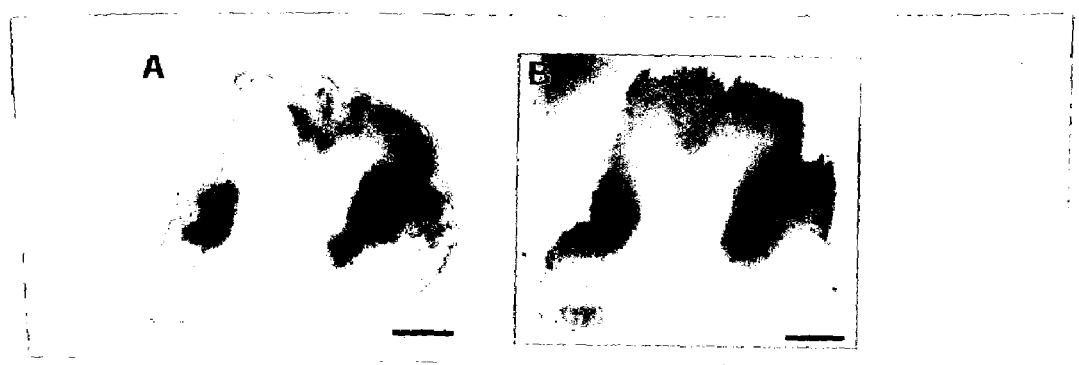
FIGS. 2A and 2B are autoradiographs that depict $^{125}$I-$A\beta_{1-40}$ and $^{125}$I-PUT-$A\beta_{1-40}$ labeling of amyloid deposits in vitro: AD temporal lobe sections were incubated with 125I-$A\beta_{1-40}$ and exposed for 6 days (A) or with $^{125}$I-PUT-$A\beta_{1-40}$ and exposed for 1 day (B). Scale bars, 5 mm.

Following immunohistochemistry (IH) to visualize the amyloid deposits, the sections were subjected to film and emulsion autoradiography to detect the presence of the $^{125}$I-A$\beta_{1-40}$ or $^{125}$I-PUT-A$\beta_{1-40}$. The sections were exposed to high-resolution autoradiographic film (Hyperfilm MP, Amersham) at −70° C. to visualize $^{125}$I-labeled amyloid deposits. FIGS. 2A-2B are the film autoradiographs. Note the presence of punctate areas of exposed film located predominantly in the regions corresponding to gray matter. This is similar to the distribution of amyloid deposits seen following IH of the tissue sections. It was possible to overlay the two for direct correspondence under the microscope. A longer duration of exposure was required for $^{125}$I-A$\beta_{1-40}$ (6 days) to achieve equal relative intensity as $^{125}$I-PUT-A$\beta_{1-40}$ (1 day), suggesting that $^{125}$I-PUT-A$\beta_{1-40}$ may have greater affinity to the amyloid deposits than $^{125}$I-A$\beta_{1-40}$.

In order to definitively correlate the IH with the iodinated peptide by colocalization, the sections were next dipped in an autoradiographic emulsion (Type NTB-3, Kodak). The slides were dipped in emulsion at 43° C. under Safelight illumination in a darkroom. The slides were chilled to solidify the emulsion and then allowed to air dry at room temperature for 3 hours in a light-proof box. The slides were exposed at 4° C. in a light-proof box with desiccant. The slides were developed with Dektol developer (Kodak) and fixed (Kodak) according to the instructions. The sections were dehydrated with successive changes of ethanol and xylene and then coverslipped with a xylene-based mounting media (CMS).

Figure 3:
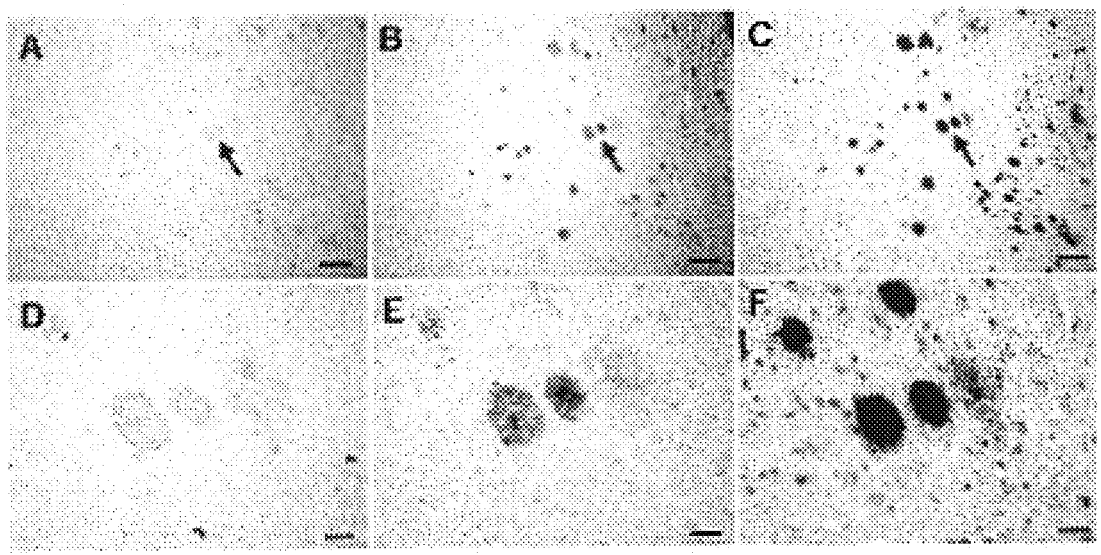
FIGS. 3A-3F are photomicrographs of $^{125}$I-$A\beta_{1-40}$ and $^{125}$I-PUT-$A\beta_{1-40}$ labeling of amyloid deposits in vitro with equivalent radioactivity.
Figure 4:
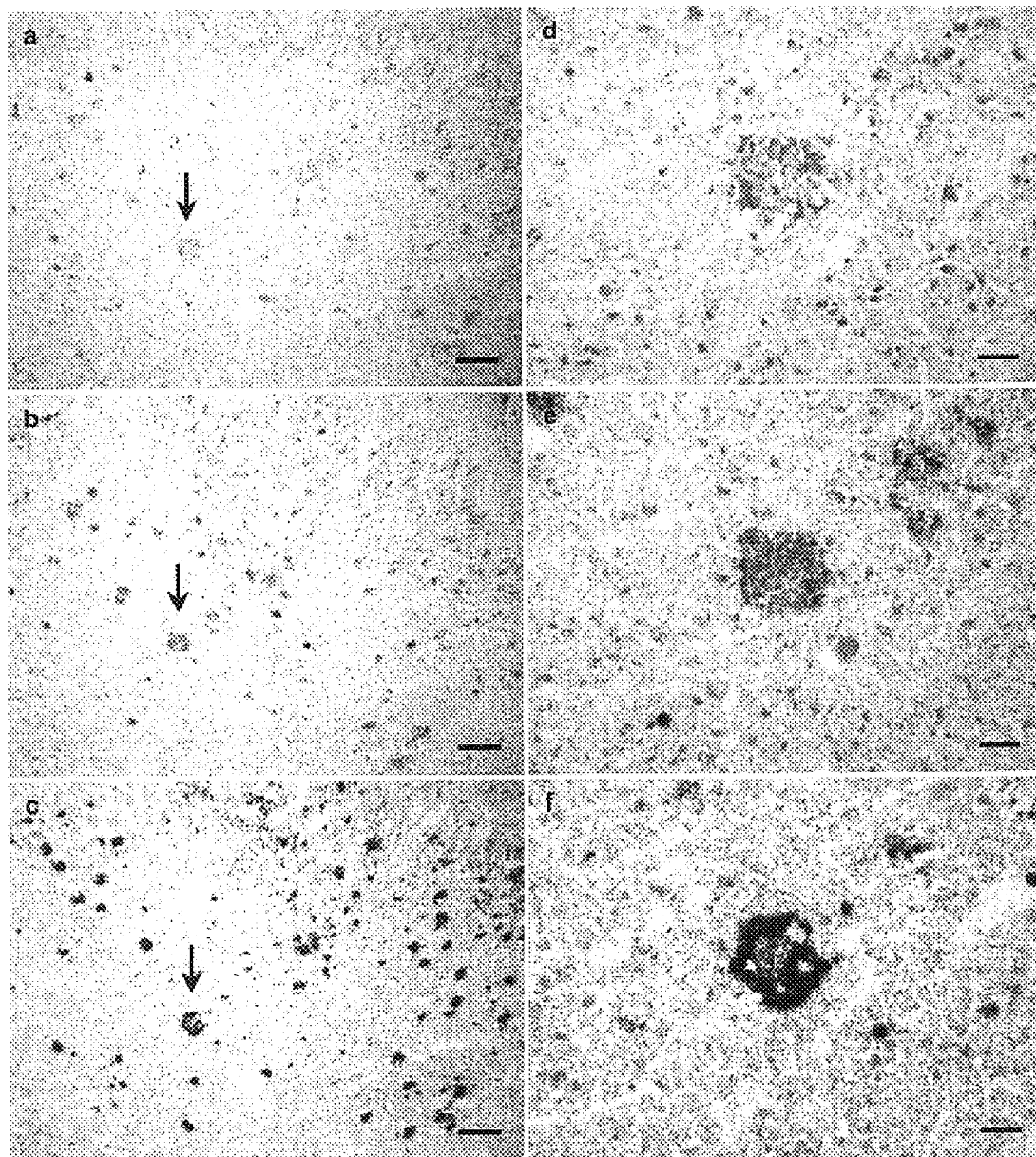
FIGS. 4A-4F are photomicrographs of $^{125}$I-$A\beta_{1-40}$ and $^{125}$I-PUT-$A\beta_{1-40}$ labeling of amyloid deposits in vitro with equivalent peptide concentration.
Figure 5:
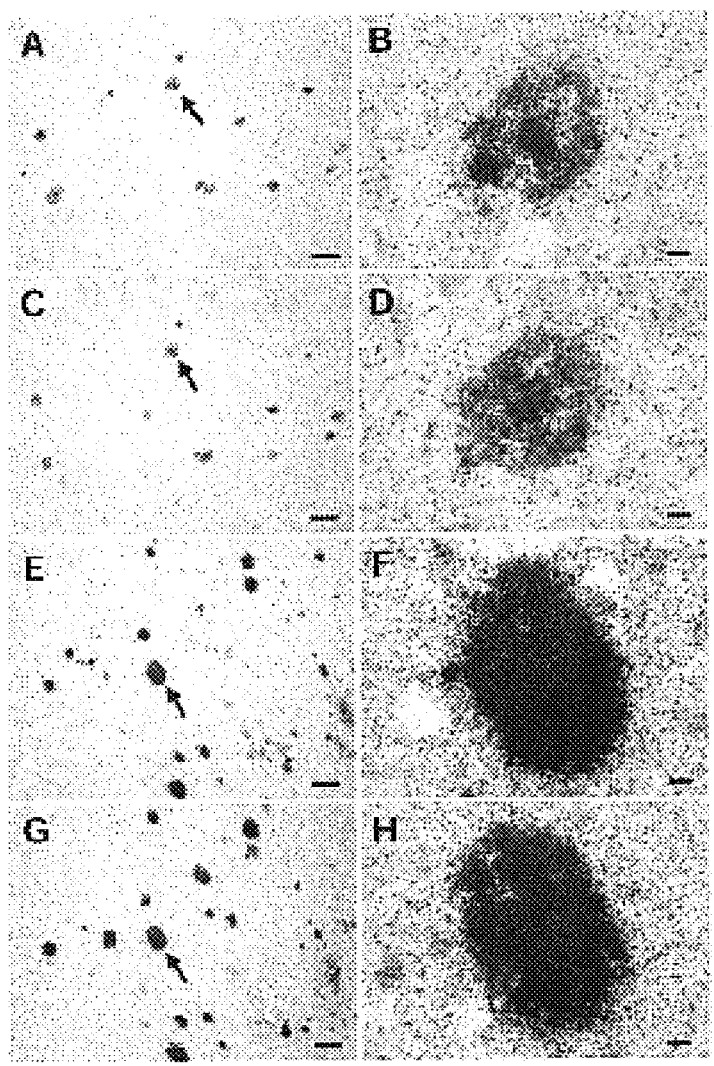
FIGS. 5A-5H are photomicrographs of $^{125}$I-$A\beta_{1-40}$ and $^{125}$I-PUT-$A\beta_{1-40}$ labeling of amyloid deposits in vitro in the absence or presence of 10-fold excess unbound putrescine.

The presence of the iodinated peptide was revealed by exposed (blackened) silver grains directly on the same tissue previously stained with anti-A$\beta$ antibody. These results are illustrated in the photomicrographs of FIGS. 3-5. FIGS. 3A-3F illustrate the binding of equal amounts of radioactivity of $^{125}$I-A$\beta_{1-40}$ and $^{125}$I-PUT-A$\beta_{1-40}$ to amyloid deposits in adjacent sections of AD temporal lobe cortex in vitro. All sections were processed for anti-A$\beta$ IH and emulsion autoradiography with an equal exposure time of 6 days. The amyloid deposits appear brown. The presence of iodinated peptide is indicated by increased density of black, exposed silver grains. The binding of both peptides is specific to the amyloid deposits due to the low density of exposed silver grains in the background. Furthermore, it seems to be selective for the dense-core, neuritic-type plaques on the left than the diffuse plaque located on the right (FIGS. 3E, F). Also note that with equal amounts of radioactivity and exposure time there is a higher density of silver grains for $^{125}$I-PUT-A$\beta_{1-40}$, suggesting that the modified peptide has a greater affinity for the neuritic plaques than $^{125}$I-A$\beta_{1-40}$. FIGS. 4A-4F illustrate the binding of equal peptide concentrations of $^{125}$I-A$\beta_{1-40}$ and $^{125}$I-PUT-A$\beta_{1-40}$ to amyloid deposits in adjacent sections of AD temporal lobe cortex in vitro. These results are similar to FIGS. 3A-3F.

Based on the result that $^{125}$I-PUT-A$\beta_{1-40}$ has a greater affinity for neuritic plaques than $^{125}$I-A$\beta_{1-40}$, an experiment was performed to determine the effect of putrescine on binding by incubating the peptides in the absence or presence of excess unbound putrescine. If putrescine also binds to amyloid, then one might expect to see decreased binding of iodinated peptide in a competitive manner in the presence of excess unbound putrescine. FIGS. 5A-5H illustrate the binding of $^{125}$I-A$\beta_{1-40}$ and $^{125}$I-PUT-A$\beta_{1-40}$ to amyloid deposits in AD temporal lobe cortex in vitro in the absence or presence of a 10-fold excess of unbound putrescine. There appears to be no appreciable effect on binding of iodinated peptide in the presence of unbound putrescine, even at 10-fold excess. This suggests that putrescine itself does not bind specifically to amyloid, but may enhance binding by some other mechanism.

In summary, in addition to increased permeability at the BBB, $^{125}$I-PUT-A$\beta_{1-40}$ also labeled amyloid deposits in vitro with greater affinity than $^{125}$I-A$\beta_{1-40}$, based on shorter exposure times or increased intensity of autoradiography emulsion. There is not a clear explanation for this observation as the addition of ten-fold excess of unbound putrescine did not decrease labeling in a competitive manner. In fact, because amyloid is highly hydrophobic and PUT-A$\beta_{1-40}$ appears to be relatively less hydrophobic than A$\beta_{1-40}$, based on a shorter retention time during HPLC, one might expect to observe decreased labeling with $^{125}$I-PUT-A$\beta_{1-40}$. Furthermore, the addition of putrescine to the structure of A$\beta_{1-40}$ could possibly block binding sites and also reduce labeling. The binding of both PUT-A$\beta_{1-40}$ and A$\beta_{1-40}$, however, appeared to be specific for dense-core, neuritic-type amyloid deposits, since no diffuse deposits were labeled and background labeling was not noticeable.

Example 3

Labeling of Amyloid Plaques In Vivo $^{125}$I-PUT-A$\beta_{1-40}$ was then tested for its ability to cross the BBB and label amyloid deposits in vivo following i.v. injection in transgenic mice that express two mutant human proteins associated with familial AD. These mice develop amyloid deposits and behavioral deficits within 12 weeks of age. Hemizygous transgenic mice (Tg2576) expressing mutant human amyloid precursor protein (APP$_{695}$) were mated with a second strain of hemizygous transgenic mice (M146L5.1) expressing mutant human presenilin 1 (PS1). Holcomb, L., et al., *Nature Med.* 4:97-100 (1998). The animals were genotyped for the expression of both transgenes by a dot blot method using a sample of mouse tail DNA. The mice were housed in a virus-free barrier facility under a 12-hour light/dark cycle, with ad lib access to food and water. All procedures performed were in accordance with NIH Guidelines for the Care and Use of Laboratory Animals. Quantitative histological analyses of amyloid deposition indicate that deposition of neuritic-type plaques occurs at a rapid rate starting around 12 weeks, reaching an amyloid burden of over 3.5% in cortex and hippocampus in one year.

These APP, PS1 transgenic mice (27 weeks of age) were catheterized in the femoral vein under general anesthesia (sodium pentobarbital, 25 mg/kg, i.p.) and injected with 200 µg of $^{125}$I-A$\beta_{1-40}$ or $^{125}$I-PUT-A$\beta_{1-40}$. One mouse was injected with $^{125}$I-A$\beta_{1-40}$ and two with $^{125}$I-PUT-A$\beta$ 1-40. After four hours, each animal was perfused with PBS and fixed with neutral-buffered, 10% formalin following an overdose with sodium pentobarbital (75 mg/kg, i.p.). After cryoprotecting in 10% and 30% sucrose in PBS, frozen sections of each brain were cut with a freezing microtome and then processed with anti-A$\beta$ IH and emulsion autoradiography for the presence of radiolabeled amyloid deposits using the same methods described above for the human AD sections.

Figure 6:
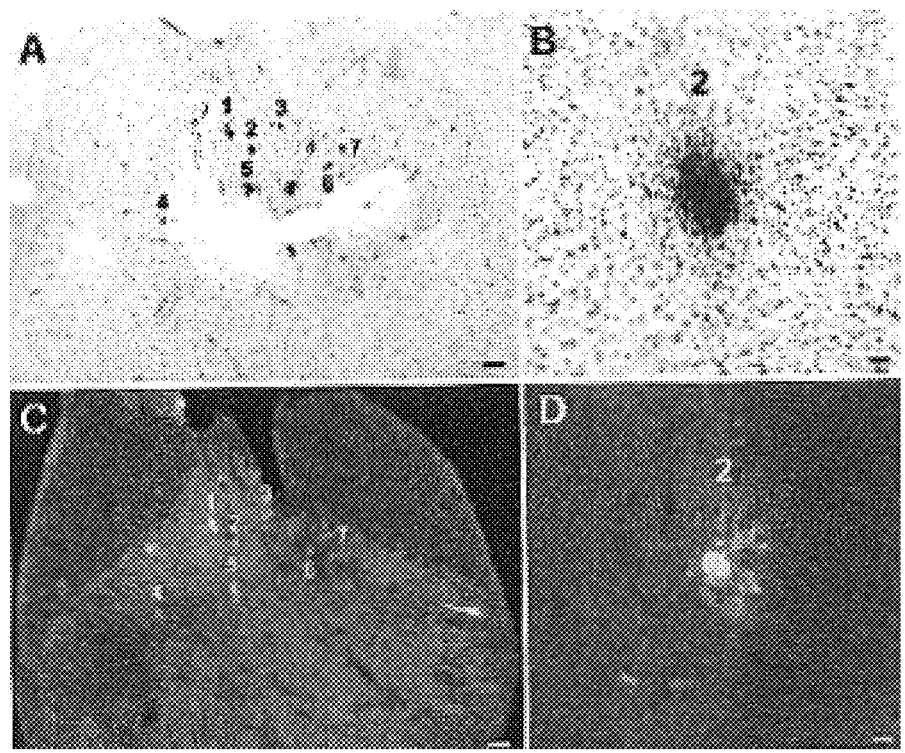
FIGS. 6A-6D are photomicrographs of $^{125}$I-PUT-$A\beta_{1-40}$ labeling of amyloid deposits in vivo in APP, PS1 transgenic mouse brain.

The results are shown in FIG. 6. FIG. 6A a photomicrograph of a section through the medial septum that exhibits several parenchymal amyloid deposits radiolabeled with $^{125}$I-PUT-A$\beta_{1-40}$. This particular section was exposed for 8 weeks, but labeled deposits could be observed after only one week of exposure. FIG. 6C illustrates a higher magnification of one of the parenchymal deposits in which the IH reaction product is visible beneath the exposed silver grains. FIG. 6B illustrates the adjacent section that was stained for thioflavin S and confirms the presence and distribution of the same parenchymal amyloid deposits. Radiolabeled parenchymal amyloid deposits were also observed in the hippocampus and fimbria/fornix of each animal. An APP, PS1 transgenic mouse injected i.v. with 200 µg of $^{125}$I-A$\beta_{1-40}$ did not exhibit labeling of any parenchymal amyloid deposits, aside from faint pial and some residual vascular labeling, with up to 12 weeks of exposure. These results demonstrate that 125I-PUT-A$\beta_{1-40}$ is able to cross the BBB and bind to amyloid deposits in vivo following i.v. administration.

In summary, these results indicate that $^{125}$I-PUT-A$\beta_{1-40}$ has increased BBB permeability compared to $^{125}$I-A$\beta_{1-40}$. Also, $^{125}$I-PUT-A$\beta_{1-40}$ retains its ability to selectively label neuritic plaques in vitro, and with greater affinity than $^{125}$I-A$\beta_{1-40}$. This binding does not seem to be affected by excess unbound putrescine. APP, PS1 transgenic mice exhibit large amounts of amyloid deposition and provide a convenient animal model to test the ability of $^{125}$I-PUT-A$\beta_{1-40}$ to label amyloid deposits in vivo. Furthermore, $^{125}$I-PUT-A$\beta_{1-40}$ labels parenchymal amyloid deposits in the brains of these mice following systemic administration. The success of these experiments supports the development of radiolabeled PUT-A$\beta_{1-40}$ as a marker of amyloid deposition for use as a diagnostic tool for AD in humans.

Example 4

Molecular Targeting of Alzheimer's Amyloid Plaques for Contrast-Enhanced MRI

The ideal MRI contrast agent for visualizing and quantifying the pathologic burden of β-amyloid plaque should have four properties: 1) be highly stable in vivo, 2) cross the BBB non-destructively following intravenous injection, 3) bind specifically to parenchymal plaques with high affinity, and 4) produce local changes in tissue contrast detectable by MRI. For human studies, this should be feasible with clinical MRI instrumentation. We describe experiments demonstrating that these properties exist in putrescine-gadolinium-amyloid-β peptide (PUT-Gd-Aβ). In these experiments, the probe was injected into live mice that were then sacrificed. MRI was performed on post-mortem specimens at very high resolution (62.5 µm$^3$) in order to prove the concept that an intravenously administered probe can selectively produce MRI-visible plaque enhancement. Although in vivo MRI of PUT-Gd-Aβ plaque enhancement represents a future experimental step that must be demonstrated before this technique can be successfully applied to the diagnosis of AD, the present study provides promising data to support the pursuit of further studies.

Materials and Methods

Synthesis of Aβ (1-40) and Modification with Gadolinium and Putrescine. Aβ (1-40) containing a metal chelating arm was synthesized on a peptide synthesizer using standard protocols for tBOC (tert-butyloxycarbonyl) chemistry. The chelating arm, diethylenetriaminepentaacetic acid (DTPA), was attached to the amino terminus of the peptide as the final step of synthesis. The peptide was purified by HPLC on a $C_{18}$ preparative column, 2.5×30 cm (Vydac Separations, Hesperia, Calif.), using linear gradients from 0-70% of acetonitrile in 0.1% trifluoroacetic acid. Gadolinium (Gd) was chelated to the DTPA-Aβ peptide using Gd (III) chloride hexahydrate (Aldrich, Milwaukee, Wis.) with a 24-hour incubation in water at pH 7.0 at room temperature. The Gd-DTPA-Aβ complex was then HPLC purified and lyophilized. Mass spectroscopy of the HPLC-purified Gd-DTPA-Aβ (Gd-Aβ) gave a mass of 4975.7, in agreement with the expected mass of 4976.6. Analytical HPLC showed a purity of >90-95%, and the molar ratio of the Aβ to Gd was 1:1. Polyamine modification was performed as described previously (Poduslo and Curran, *J. Neurochem.* 66:1599-1609 (1996a); Poduslo and Curran, *J. Neurochem.* 67:734-741 (1996b); Wengenack, et al., *Brain Res.* 767:128-135 (1997); Poduslo, et al, *J Neurochem.* 71:1651-1660 (1998); Poduslo, et al., *Ann. Neurol.* 48:943-947 (2000). One modification to the procedure was that the PUT-Gd-Aβ was dialyzed against 20 µM gadolinium chloride instead of distilled water. This was done as a precaution to protect against the loss of any of the chelated Gd from the peptide, which was later determined to be unnecessary.

PS and $V_p$ Determination in Mice. PS/$V_p$ measurements were performed as described previously (Poduslo and Curran, supra (1996a); Poduslo and Curran, supra (1996b); Wengenack, et al., supra (1997); Poduslo, et al., supra (1998); Poduslo, et al., supra (2000); Poduslo, et al., *Neurobiol. Dis.* 8:555-567 (2001). All procedures performed were in accordance with NIH Guidelines for the Care and Use of Laboratoty Animals. This involved the IV bolus injection technique in which a bolus of PBS containing $^{125}$I-labeled protein was rapidly injected into the catheterized femoral vein of anesthetized mice (sodium pentobarbital, 25 mg/kg, IP). Blood was sampled from the femoral artery at several intervals during the next 15 minutes. Whole blood was sampled directly, using heparinized micro-hematocrit capillary tubes and TCA extracted. The supernatant was separated from the pellet and both were counted in a gamma counter. The radioactivity in the pellet was expressed as a percentage of the total radioactivity found in both the pellet and supernatant. An aliquot of the peptide labeled with $^{131}$I was then injected into the femoral vein 15 seconds prior to sacrifice of the animal to serve as a measure of residual plasma volume ($V_p$; μl/g). After collection of the final blood sample, the anesthetized animal was sacrificed. Several brain regions were dissected and assayed for $^{125}$I and $^{131}$I radioactivity in a two-channel gamma counter (Cobra II, Packard) with the activity corrected for background and crossover of $^{131}$I activity into the $^{125}$I channel. The permeability coefficient x surface area products (PS; $10^{-6}$ ml/g/s) were then calculated using the $V_p$ as a measure of residual plasma volume based on equations that have been discussed in detail elsewhere (Poduslo and Curran, supra (1996a); Poduslo and Curran, supra (1996b); Wengenack, et al., supra (1997); Poduslo, et al., supra (1998); Poduslo, et al., supra (2000); Poduslo, et al., supra (2001). Statistical evaluations of PS and $V_p$ were performed using ANOVA followed by Bonferroni multiple comparisons.

Labeling of AD Amyloid Plaques In Vitro with Putrescine- and Gadolinium-Labeled Aβ. HPLC-purified $^{125}$I-Gd-Aβ 1-40 and $^{125}$I-PUT-Gd-Aβ 1-40 were incubated with sections of unfixed AD temporal lobe cortex. Three sections were incubated with either $^{125}$I-Gd-Aβ 1-40, $^{125}$I-PUT-Gd-Aβ 1-40, or vehicle using the same procedure we used previously (Wengenack, et al., Nat. Biotechnol. 18:868-872 (2000a). Briefly, the sections were incubated for 3 hours with 100 pM $^{125}$I-Gd-Aβ1-40 or $^{125}$I-PUT-Gd-Aβ 1-40, or alone in 250 μl of TBS containing 0.1% BSA, 0.6 mg/ml magnesium chloride, 0.04 mg/ml bacitracin, 0.002 mg/ml chymostatin, and 0.004 mg/ml leupeptin. The sections then underwent immunohistochemistry (IH) for amyloid using an anti-Aβ monoclonal mouse antibody (4G8, 1:1000, Signet Laboratories, Dedham, Mass.). Next, the sections were dipped in an autoradiographic emulsion (Type NTB-3, Kodak, Rochester, N.Y.) for direct comparison of $^{125}$I-labeled amyloid deposits to anti-Aβ IH. The slides were dipped in emulsion, exposed, and developed according to the instructions. The sections were dehydrated with successive changes of ethanol and xylene and then coverslipped.

Catheterization and Injection of Mice. The double transgenic mice were cross-bred in-house. Hemizygous transgenic mice (mouse strain: C57B6/SJL; I.D.# Tg2576) expressing mutant human APP$_{695}$ containing a double mutation (K670N, M671L) (Hsaio, et al., Science 274:99-102 (1996) were mated with a strain of homozygous transgenic mice (mouse strain: Swiss Webster/B6D2; I.D.# M146L6.2) expressing mutant human PS1 containing a single mutation (M146L) (Holcomb, et al., Nat. Med. 4:97-100 (1998). Each animal was catheterized via the femoral vein under general anesthesia (sodium pentobarbital, 25 mg/kg, IP). Two mice (one non-transgenic and one APP-PS1) injected with PBS received a total volume of 200 μl over the course of 15 minutes. A total of nine mice (two nontransgenic, five APP-PS1, and two APP) were injected with PUT-Gd-Aβ, receiving doses ranging from 0.4-2.0 mg. One mouse was injected with 0.4 mg of Gd-Aβ. Another mouse was injected with the molar equivalent of Gd-DTPA (0.1 mg, Magnevist (gadopentetate dimeglumine), Berlex Laboratories). After four hours, each animal was perfused with PBS and fixed with neutral-buffered, 10% formalin following an overdose with sodium pentobarbital (75 mg/kg, IP). The brain was removed and fixed further in formalin overnight and then equilibrated in 0.1 M sodium phosphate, pH 7.4 for 24 hours. The right hemisphere was embedded vertically in 2% agar in a 10-mm O.D. glass tube for MRI.

Magnetic Resonance Imaging. MRI was performed with a Bruker Avance DRX-300, 89-mm vertical bore spectrometer. The glass tube containing the embedded mouse brain was inserted into a 10-mm diameter RF coil. T2W and T1W imaging sequences were performed with the following parameters: field of view of 1.6 cm along the z (vertical magnet) axis and 0.8 cm along the other two orthogonal axes; data acquisition matrix size of 256 (along the z axis)×128×128 resulting in cubic voxels 62.5 μm in all dimensions. The signal was read out along the z-axis direction at a bandwidth of 50 kHz. A T2W image volume with TR=3000 ms and TE=100 ms was obtained in 13 hours, 52 minutes. A T1W image volume with TR=400 ms and TE=8 ms and 8 signal averages was obtained in 14 hours, 42 minutes.

Thioflavin S Staining and Histological Correlation. After MRI, the bottom of the glass MRI tube was cut off and the agar and hemisphere extruded. The agar was then carefully cut away from the hemisphere. A 5-mm thick block of agar was left attached to the posterior portion of the hemisphere as a base for mounting to the microtome platform in order to maintain the same orientation of the hemisphere as in the MRI scan. After cryoprotecting in sucrose, frozen coronal sections (30 μm) of each hemisphere were cut with a sliding microtome throughout the whole extent of the cerebral cortex. The sections were mounted on slides, dried, and then stained with fresh, filtered, aqueous 1% thioflavin S. The thioflavin S-positive β-amyloid deposits were visualized using a confocal laser scanning microscope. Confocal images were obtained using an argon/krypton laser and settings for fluorescein isothiocyanate at an excitation wavelength of 488 nm and emission of 520 nm.

In order to correlate them to the MR images, images of the individual histologic sections were combined to create a digitized 3D volume of the specimen using an image analysis software package (Robb, 3D Imaging in Medicine, pp. 333-361 (1990). The through-plane voxel dimension was equal to 62.5 μm in the MR scans and 30 μm in the histologic sections. In order to match the through-plane resolution of the histologic and MR images, every other 30-μm histological section was used. The 3D T2W MRI volume was then spatially matched to the digitized histologic volume using common anatomic landmarks, for example the anterior commissure. The rigid-body transformation matrix derived from the anatomic matching procedure was saved and applied to both the T2W and T1W MR image volumes which were resampled in the space of the digitized histologic volume using sinc interpolation. The T2W and T1W MR volumes were in perfect spatial registration with each other a priori because the geometric parameters of the T2W and T1W acquisition protocols were identical.

Results

BBB Permeability of Putrescine- and Gadolinium-Labeled Aβ Peptide. Our previous studies have demonstrated that modification of proteins with endogenously occurring polyamines such as putrescine dramatically increases their permeability at the BBB (Poduslo and Curran, supra (1996a); Poduslo and Curran, supra (1996b); Wengenack, et al., supra (1997); Poduslo, et al., supra (1998): Poduslo, et al., supra (2000). In addition, we have demonstrated that putrescine-modified Aβ has a highly significant 1.9-2.3 fold increase in the permeability coefficient-surface area product (PS) in six different brain regions as compared to the native, unmodified Aβ (Wengenack, et al., supra (2000a). It was possible, however, that Gd labeling for MRI contrast purposes would significantly reduce the BBB permeability of PUT-Aβ. In order to test this hypothesis, the BBB permeabilities of the Gd-labeled and PUT- and Gd-labeled Aβ peptides were measured in non-transgenic mice.

The BBB permeabilities of Gd-labeled Aβ (Gd-Aβ) and PUT- and Gd-labeled Aβ (PUT-Gd-Aβ) were quantified in different brain regions of non-transgenic mice using an IV bolus injection technique with correction for the residual blood volume ($V_p$) (Table 2).

TABLE 2

PS and $V_p$ of Aβ, PUT-Aβ, Gd-Aβ, and PUT-Gd-Aβ at the BBB in Non-Transgenic Mice

| Brain Region | Aβ (n = 14) | PUT-Aβ (n = 8) | RI | P | Gd-Aβ (n = 8) | RI | P | PUT-Gd-Aβ (n = 7) | RI | P |
|---|---|---|---|---|---|---|---|---|---|---|
| PS | | | | | | | | | | |
| Cortex | 52.3 ± 3.4 | 125.7 ± 7.6 | 2.4 | *** | 32.4 ± 3.8 | 0.6 | ns | 91.3 ± 9.5 | 1.7 | *** |
| Caudate-Putamen | 41.0 ± 3.2 | 99.6 ± 4.6 | 2.4 | *** | 23.5 ± 3.1 | 0.6 | ns | 60.0 ± 9.0 | 1.5 | * |
| Hippocampus | 48.7 ± 3.2 | 105.5 ± 6.9 | 2.2 | *** | 30.5 ± 3.2 | 0.6 | * | 84.2 ± 6.8 | 1.7 | *** |
| Thalamus | 50.8 ± 3.4 | 123.3 ± 6.5 | 2.4 | *** | 32.4 ± 3.7 | 0,6 | ns | 83.1 ± 12.5 | 1.6 | ** |
| Brain Stem | 61.6 ± 4.1 | 155.1 ± 19.0 | 2.5 | *** | 45.3 ± 5.2 | 0.7 | ns | 125.8 ± 8.9 | 2.0 | *** |
| Cerebellum | 65.5 ± 4.5 | 159.2 ± 9.4 | 2.4 | *** | 42.9 ± 4.9 | 0.7 | ns | 113.3 ± 12.5 | 1.7 | *** |
| $V_p$ | | | | | | | | | | |
| Cortex | 14.3 ± 1.0 | 40.4 ± 2.5 | 2.8 | *** | 16.8 ± 0.6 | 1.2 | ns | 58.2 ± 2.7 | 4.1 | *** |
| Caudate-Putamen | 9.8 ± 0.9 | 31.5 ± 1.9 | 3.2 | *** | 9.1 ± 0.5 | 0.9 | ns | 43.4 ± 2.2 | 4.4 | *** |
| Hippocampus | 15.6 ± 1.3 | 35.9 ± 2.9 | 2.3 | *** | 15.4 ± 0.7 | 1.0 | ns | 52.2 ± 3.3 | 3.3 | *** |
| Thalamus | 13.0 ± 0.9 | 40.5 ± 2.7 | 3.1 | *** | 15.8 ± 0.6 | 1.2 | ns | 58.8 ± 2.6 | 4.5 | *** |
| Brain Stem | 17.3 ± 1.3 | 46.3 ± 3.0 | 2.7 | *** | 19.3 ± 1.2 | 1.1 | ns | 63.5 ± 3.6 | 3.7 | *** |
| Cerebellum | 20.8 ± 1.6 | 54.5 ± 2.1 | 2.6 | *** | 22.4 ± 1.0 | 1.1 | ns | 73.4 ± 3.7 | 3.5 | *** |

PS: Permeability coefficient-surface area product (ml/g/s × $10^{-6}$, $\bar{x}$ ± SEM) determined with $^{125}$I-Aβ derivatives over the course of 15 min and corrected for $V_p$.
$V_p$: Residual brain region blood volume (μl/g, $\bar{x}$ ± SEM) determined with $^{131}$I-Aβ derivatives given 15 sec prior to end of experiment.
RI: relative increase versus Aβ.
P: ANOVA with Bonferroni mulitple comparisons versus Aβ:
ns—not significant (P > 0.05);
*P < 0.05;
**P < 0.01;
***P < 0.001.

Polyamine modification resulted in a significant 2.2-2.5 fold increase in the PS values. Not surprisingly, when Aβ was labeled with gadolinium, there was a decrease in the PS value in five of the six brain regions, however, this was of non-significant magnitude. Interestingly, after putrescine modification of the Gd-Aβ, this decrease in permeability was partially rescued. These PS values were all highly significantly increased by 1.5-2.0 fold compared to Aβ and represented only a 19-40% decrease in the PS values compared to PUT-Aβ in the different brain regions.

The $V_p$ values for Aβ, PUT-Aβ, Gd-Aβ, and PUT-Gd-Aβ were also measured in six different brain regions in non-transgenic mice (Table 2). After putrescine modification of Aβ, the $V_p$ values increased significantly by 2.3-3.2 fold. These increases are probably the result of the large increases in the PS values observed for PUT-Aβ with some of the peptide crossing the BBB even during the short, 15-second time interval for the administration of the second isotope. This observation has been made for several proteins that have high BBB permeabilities and suggests that the PS values are an underestimation. The $V_p$ values for Gd-Aβ were not significantly different from those of Aβ. The PUT-Gd-Aβ, however, showed a significant increase that ranged from 3.3-4.5 fold compared to Aβ. In summary, gadolinium modification had a relatively small effect on the BBB permeability of Aβ, which was rescued by polyamine modification. This high permeability should allow it to access the brain's parenchyma after systemic administration in the same manner as has been described for radioiodinated PUT-Aβ (Wengenack, et al., supra (2000a). Although the permeability measurements performed in the present study do not directly measure the amount of PUT-Gd-Aβ in the brain, in a previous study (Wengenack, et al., supra (2001 a) we measured the amount of radiolabeled PUT-Aβ in PBS-perfused brain following IV injection. There was greater than 10-fold more $^{125}$I-PUT-Aβ present in the brain compared to $^{125}$I-Aβ (0.35% vs. 0.03%, respectively) four hours after injection of equal doses. This not only confirms the higher permeability values of PUT-Aβ compared to Aβ, but also indicates that a substantial fraction of the injected dose enters the brain. Since PUT-Gd-Aβ exhibits similar increases in permeability values it is likely that it also enters the brain in sufficient quantity.

Labeling of AD Amyloid Plaques In Vitro with Putrescine- and Gadolinium-Labeled Aβ Peptides. The next step was to determine if Gd modification had any effect on the ability of Aβ or PUT-Aβ to label β-amyloid plaques in human AD brain sections in vitro, as reported previously by us (Wengenack, et al., supra (2000a). Our results showed the detection of radiolabeled Gd-Aβ or PUT-Gd-Aβ binding to plaques in vitro in AD brain tissue processed with anti-Aβ immunohistochemistry and emulsion autoradiography. As indicated, $^{125}$I-PUT-Gd-Aβ is able to bind to plaques, and at a higher level than $^{125}$I-Gd-Aβ. This is apparent because $^{125}$I-PUT-Gd-Aβ required an exposure time of only one day, whereas the $^{125}$I-Gd-Aβ required an exposure time of nine days following application of equal amounts of radioactivity. The putrescine modification, therefore, allows for a dramatic increase in the binding of Aβ to plaques even in the presence of the gadolinium modification. These studies demonstrate that PUT-Gd-Aβ retains the same plaque binding properties as described previously for PUT-Aβ (Wengenack, et l., supra (2000a), and therefore could likely function as an MRI probe to target plaques after IV administration.

MRI-Histologic Correlation in APP-PS1 Mice Injected with PUT-Gd-Aβ. The main objective of this study was to test the hypothesis that enhanced MRI contrast features consistent with selective binding of PUT-Gd-Aβ to β-amyloid plaques are present after IV administration in AD transgenic mice. Transgenic mice that express two mutant human proteins associated with familial AD, amyloid precursor protein (APP) and presenilin 1 (PS1), were used in these experiments (Holcomb, et al., *supra* (1998). These mice develop β-amyloid deposits and behavioral deficits within 12 weeks of age. Amyloid burden increases an average of 179-fold from 12 to 52 weeks of age (0.02% to 3.57%) in the cortex and hippocampus (Wengenack, et al., *supra* (2000b). Therefore, these mice provide an appropriate animal model to test this hypothesis.

APP-PS1 transgenic mice (1 year of age) were injected IV with PUT-Gd-Aβ. After four hours, each mouse was sacrificed, perfused, and its brain removed for imaging. T2- and T1-weighted (T2W and T1W, respectively) MR imaging sequences were performed at 7 Tesla. After MRI, the hemispheres were sectioned, stained with thioflavin S, and then correlated with the MR images. Once the histologic and MR volumes had been registered into the same spatial coordinate system, a linked cursor was used to identify common coordinate positions in the histologic specimen and the two MR image volumes. The ability to position the cursor at any location in one image and visualize that precise anatomic location in the other registered image volumes was used to identify and compare the appearance of plaques that were captured equivalently on the thioflavin S and MR images. A photomicrograph of thioflavin S-stained histologic section and the corresponding T2W and T1W MR images shows numerous focal areas. Numerous focal areas of accelerated T2 relaxation are visible as dark spots on the T2W image in regions with abundant thioflavin S-positive plaques, such as the cortex and hippocampus. Although it was impossible to obtain a direct one-to-one correlation between every thioflavin S-positive plaque in the histological section and every area of accelerated T2 relaxation, many plaques could be unequivocally matched and five representative plaques are labeled. There were also many focal areas of accelerated T1 relaxation visible as bright spots on the T1W images that directly corresponded to plaques in the thioflavin S section. These results were typical for all the APP-PS1 mice injected with PUT-Gd-Aβ. This pattern suggested that PUT-Gd-Aβ crossed the BBB, labeled amyloid plaques, and could be detected by MRI.

MRI-Histologic Correlation in a Non-Transgenic Mouse. We next wished to test the hypothesis that the features visible on the T2W and T1W MR images described in the previous section were specific for amyloid plaques in the transgenic mouse. The same procedures for animal preparation, MRI, and MRI-histologic correlation described in the previous section were carried out on a non-transgenic mouse injected with phosphate-buffered saline (PBS). As expected, the thioflavin S sections showed no staining, and no evidence of focal areas of accelerated T1 relaxation were observed on the corresponding MR sections. Although focal areas of accelerated T2 relaxation were not apparent in the cortex, some were present in the striatum, illustrating that this is not an imaging feature specific for amyloid plaques. A non-transgenic mouse injected with PUT-Gd-Aβ yielded the same results. We concluded that the focal areas of accelerated T1 relaxation observed in transgenic mice injected with PUT-Gd-Aβ were enhanced plaques and not a non-specific feature of IV-injected PUT-Gd-Aβ.

MRI-Histologic Correlation in an APP-PS1 Mouse injected with PBS. We next performed a control experiment in an APP-PS1 transgenic mouse injected with PBS. This experiment was done for two reasons. First, we wished to test the hypothesis that plaques in this AD transgenic mouse model had the same MR contrast properties without the addition of a contrast agent as had been demonstrated in human ex vivo tissue (Benveniste, et al., *Proc. Natl. Acad. Sci. USA* 96:14079-14084 (1999). Second, we had to establish the baseline appearance of plaques on T2W and T1W MR images in the absence of the PUT-Gd-Aβ contrast agent. Animal preparation, MRI, and histologic correlation were performed as described above. Focal areas of accelerated T2 relaxation were present in the T2W image that corresponded to plaques in the thioflavin S section, but none were apparent in the T1W image. Plaques therefore accelerated the T2 relaxation rate, but had no appreciable effect on the T1 relaxation of brain tissue in the absence of PUT-Gd-Aβ. This further supports the observation in the PUT-Gd-Aβ-injected APP-PS1 mice that focal areas of accelerated T1 relaxation represent plaques labeled with PUT-Gd-Aβ.

MRI-Histologic Correlation in an APP-PS1 Mouse Injected with Gd-DTPA. We also wished to rule out the possibility that the MR contrast properties observed with IV injection of PUT-Gd-Aβ were a non-specific effect of intravascular Gd in the APP-PS1 mouse. In order to test this hypothesis, an APP-PS1 transgenic mouse was injected IV with a molar equivalent amount of Gd-DTPA. The resulting T2W images showed the expected focal areas of T2 acceleration that corresponded to plaques. No evidence of T1 plaque enhancement was seen in the T1W images, however. This experiment confirmed our hypothesis that plaque enhancement is a specific feature of PUT-Gd-Aβ and not a non-specific effect of intravascular Gd.

MRI-Histologic Correlation in an APP-PS1 Mouse Injected with Gd-Aβ. The first two experiments of this study demonstrated that both BBB transport and binding of Gd-Aβ to plaques is greatly enhanced by PUT modification. However, since Gd-Aβ without the addition of putrescine was also shown to label plaques in vitro, albeit at a much lower level, in a final experiment we tested the hypothesis that PUT modification of the Gd-Aβ molecule is necessary to obtain observable T1 relaxation of plaques following IV injection. In an APP-PS1 transgenic mouse injected IV with Gd-Aβ, accelerated T2 relaxation was observed in plaques as expected, but no significant plaque enhancement was observed on T1W images. Based on this series of primary and control experiments, we conclude that the accelerated T1 relaxation observed could only be the result of the presence of PUT-Gd-Aβ in the plaques.

Quantitative Voxel Intensity Measurements. Although the images themselves seem convincing enough to prove the hypothesis that PUT-Gd-Aβ specifically labels plaques in vivo and is detectable by MRI, quantitative measurements were also performed. Intensity measurements were performed on plaques represented equivalently in the histologic and T2W images in order to quantitate the T2 and T1 contrast properties of individual plaques under varying experimental conditions. The plaque-to-background voxel intensity ratios (PBR) for individual plaques were calculated as the minimum (T2) or maximum (T1) intensity value within a region of interest (ROI) drawn around each plaque, divided by the intensity of adjacent, normal appearing background tissue. The background intensity was calculated as the average of the mean intensities of three 4-voxel$^2$ regions sampled adjacent to each plaque. To eliminate any bias in quantifying plaque contrast enhancement, plaques measured were visible in both the thioflavin S image and the T2W image without prior viewing of the T1W image. The ROI was then positioned in the T1W image at the same coordinates as in the T2W image and the maximum intensity recorded. The PBRs were significantly decreased for the T2W images and significantly increased for the T1W images in APP-PS1 mice injected with PUT-Gd-Aβ compared to APP-PS1 mice injected with PBS (Table 3).

TABLE 3

Plaque-to-Background Voxel Intensity Ratios and Contrast-to-Noise Ratios of Amyloid Plaques Compared to Background in T2 and T1 MRI Scans of AD Transgenic Mouse Brain

|  | T2 | | T1 | |
|---|---|---|---|---|
| Probe | PBR[a] | CNR[b] | PBR[a] | CNR[b] |
| PBS | 0.59 ± 0.03 | −4.95 ± 0.31 | 1.02 ± 0.01 | 0.76 ± 0.26 |
| Gd-Aβ | 0.48 ± 0.03 | −6.18 ± 0.43 | 1.03 ± 0.01 | 1.71 ± 0.28 |
| PUT-Gd-Aβ | 0.29 ± 0.03*** | −8.95 ± 0.53*** | 1.24 ± 0.04*** | 7.13 ± 1.03*** |

[a]The plaque-to-background voxel intensity ratios (PBR, mean ± SEM, n = 15) were calculated as the minimum (T2) or maximum (T1) intensity value within a region drawn around each plaque divided by the background intensity, which was the average of the mean intensities of three 4-voxel regions sampled adjacent to each plaque. Cubic voxel size = 62.5 μm on a side.
***P < 0.001 vs. PBS by Bonferroni post-hoc comparison performed following one-way ANOVAs:
T2—[$F(2, 44) = 28.98$; $P < 0.0001$],
T1—[$F(2, 44) = 29.31$; $P < 0.0001$].
[b]The contrast-to-noise ratios (CNR, mean ± SEM, n = 15) were calculated as the minimum (T2) or maximum (T1) intensity value of each plaque minus the background intensity divided by the standard deviation of the noise. The noise was measured in a 144-μm$^2$ area of agar adjacent to the tissue.
***P < 0.001 vs. PBS by Bonferroni post-hoc comparison performed following one-way ANOVAs:
T2—[$F(2, 44) = 29.32$; $P < 0.0001$],
T1—[$F(2, 44) = 22.38$; $P < 0.0001$].

IV injection of Gd-Aβ slightly decreased the T2 PBRs (not significantly, however), but had no effect on the T1 PBRs (Table 3).

Plaque-to-background tissue contrast-to-noise ratios (CNR) were also calculated. CNRs were calculated as the minimum (T2) or maximum (T1) intensity value of each plaque minus the background tissue intensity divided by root mean square (RMS) noise. RMS noise was measured as the standard deviation in a region of interest placed over the agar adjacent to the tissue in each image. Like the PBRs, the CNRs were significantly decreased for the T2 images and significantly increased for the T1 images in APP-PS1 mice injected with PUT-Gd-Aβ compared to APP-PS1 mice injected with PBS (Table 3). The CNRs for the T1 images, however, showed a more dramatic increase in the PUT-Gd-Aβ-injected mice compared to the PBRs (4.2-9.4 fold vs. 1.2-fold). These quantitative results are best explained by: 1) transport of the intact PUT-Gd-Aβ molecule across the BBB, 2) binding of the complex specifically to plaques, and 3) enhancement of both T2 and T1 relaxation of tissue water by the complex in plaques.

In order to further support the likelihood of successfully visualizing labeled plaques in vivo, we developed an imaging metric that crudely approximates histologic measures of labeled tissue volume fraction. Measurements were performed on the T1W images of the APP-PS1 mouse injected with PUT-Gd-Aβ. We measured the number of pixels in cortical ROIs whose signal intensity exceeded 4 S.D. above the mean intensity of normal background cortical tissue. An 812.5×812.5 μm ROI was selected. Within this larger ROI, a smaller region (125.0×187.5 μm) of normal appearing (background) cortical tissue was selected and its mean signal intensity and S.D. measured. Pixels whose intensity was ≧4 S.D. above this mean were then regarded to lie outside (above) the normal distribution of pixel intensities of non-enhanced tissue. Within the 812.5×812.5 μm cortical ROI, we then measured the proportion of pixels whose signal intensity exceeded the normal range by 4 S.D. in 10 consecutive T1W images with the ROI in the same position in the hemisphere. This proportion was interpreted to represent the volume fraction of labeled (i.e., enhanced) plaques. Pixels that met this criteria clearly corresponded to enhanced plaques. The mean (±S.D.) proportion of pixels within the ROI whose intensity exceeded the 4-S.D. threshold across 10 images was 9.9% (±8.9%). We interpret this to indicate that roughly 10% of the cortical tissue volume in this mouse was occupied by plaque that enhanced to a sufficient degree that it was easily distinguished from normal background tissue.

The invention claimed is:

1. A method for detecting parenchymal plaque deposits in the brain of a living mammal, said method comprising:
    a) administering an amount of a polypeptide to said mammal effective to detectably bind to said parenchymal deposits, wherein said polypeptide is labeled with a contrast agent and is polyamine modified, and wherein said polypeptide has specific binding affinity for said deposits; and
    b) detecting said polypeptide bound to said deposits, said detecting step comprising acquiring nuclear magnetic resonance image data and reconstructing an image therefrom.

2. The method of claim 1, wherein said deposits are β-amyloid plaques.

3. The method of claim 2, wherein said polypeptide is a β-amyloid peptide.

4. The method of claim 3, wherein said β-amyloid peptide is β-amyloid peptide$_{1-40}$.

5. The method of claim 1, wherein said polyamine is putrescine.

6. The method of claim 1, wherein said contrast agent is selected from the group consisting of Gd, dysprosium, and iron.

7. The method of claim 1, wherein said polypeptide is administered intravenously.

8. The method of claim 1, wherein magnetic resonance imaging comprises obtaining a T2-weighted image.

9. The method of claim 8, wherein deposits are detected by a reduced average signal intensity in said T2-weighted image relative to the average signal intensity in a T2-weighted image of a control region lacking extracellular deposits.

10. The method of claim 1, wherein magnetic resonance imaging comprises obtaining a T1-weighted image.

11. The method of claim 10, wherein extracellular deposits are detected by an elevated average signal intensity in said T1-weighted image relative to the average signal intensity in a control T1-weighted image of a control region lacking extracellular deposits.

12. A method for producing an image with a magnetic resonance imaging (MRI) system which indicates parenchymal plaques in the brain of a subject, the steps comprising:
    a) acquiring a reference image data set of the brain with the MRI system;
    b) injecting into the subject's vascular system a contrast agent comprised of a labeled polypeptide having a specific binding affinity for said plaques and being polyamine modified to enhance transit through and exit from capillary endothelial cells to the brain parenchyma;

c) waiting for a time period sufficient for the contrast agent to bind to said parenchymal plaques and for unbound contrast agent to diffuse in the subject;

d) acquiring a contrast enhanced image data set of the brain with the MRI system; and e) reconstructing an image of the brain which indicates at each of its image pixels the difference in NMR signal magnitude between the contrast enhanced image data set and the reference image data set.

13. The method as recited in claim 12 in which the label is a material which alters the T1 relaxation constant of surrounding spins and steps a) and d) are performed using a pulse sequence that directs the MRI system to acquire T1 weighted image data.

14. The method as recited in claim 13 in which the label material includes gadolinium.

15. The method as recited in claim 12 in which step c) includes:

i) removing the subject from the MRI system during the time period;

ii) placing the subject back into the MRI system; and iii) aligning the subject such that the contrast enhanced image data is registered with the reference image data.

16. The method as recited in claim 12 in which the label is a material which alters the T2 relaxation constant of surrounding spins and steps a) and d) are performed using a pulse sequence that directs the MRI system to acquire T1 weighted image data.

17. The method as recited in claim 16 in which the label material includes gadolinium.

18. The method of claim 1 where said polypeptide is labeled with a radioisotope selected from a group consisting of $^{123}$I, $^{18}$F, $^{111}$In, $^{67}$Ga, and $^{99m}$Tc.

19. The method of claim 2 wherein said polypeptide is an isolated antibody having specific binding affinity for a β-amyloid peptide wherein said antibody is polyamine modified and labeled with a radioisotope or contrast agent suitable for diagnostic imaging.

* * * * *